(12) United States Patent
Rah et al.

(10) Patent No.: US 9,200,300 B2
(45) Date of Patent: Dec. 1, 2015

(54) **MICROORGANISMS OF *CORYNEBACTERIUM* WHICH CAN UTILIZE XYLOSE AND METHOD FOR PRODUCING L-LYSINE USING SAME**

(71) Applicant: CJ CHEILJEDANG CORPORATION, Seoul (KR)

(72) Inventors: So Yeon Rah, Seoul (KR); Lan Huh, Seoul (KR); Chang Gyeom Kim, Seoul (KR); Kwang Ho Lee, Seoul (KR); Jun Ok Moon, Seoul (KR); Kyung Han Lee, Seoul (KR); Jin Seok Sung, Yongin-si (KR); Hyung Joon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/371,653

(22) PCT Filed: Jan. 10, 2013

(86) PCT No.: PCT/KR2013/000221
§ 371 (c)(1),
(2) Date: Jul. 10, 2014

(87) PCT Pub. No.: WO2013/105802
PCT Pub. Date: Jul. 18, 2013

(65) Prior Publication Data
US 2014/0377816 A1    Dec. 25, 2014

(30) Foreign Application Priority Data
Jan. 10, 2012    (KR) .......................... 10-2012-0003133

(51) Int. Cl.
| | | |
|---|---|---|
| *C12P 13/08* | (2006.01) | |
| *C12N 1/21* | (2006.01) | |
| *C12N 9/90* | (2006.01) | |
| *C12N 9/12* | (2006.01) | |
| *C12N 9/92* | (2006.01) | |

(52) U.S. Cl.
CPC ............... *C12P 13/08* (2013.01); *C12N 9/1205* (2013.01); *C12N 9/92* (2013.01); *C12Y 207/01017* (2013.01); *C12Y 503/01005* (2013.01)

(58) Field of Classification Search
CPC .......... C12N 1/20; C12N 9/1205; C12N 9/90; C12N 9/92; C12Y 503/01005; C12Y 207/01017; C12P 13/08
USPC .............................. 435/252.32, 233, 194, 115
See application file for complete search history.

(56) References Cited

U.S. PATENT DOCUMENTS

| | | |
|---|---|---|
| 2006/0216804 A1 | 9/2006 | Karhumaa |
| 2009/0246846 A1* | 10/2009 | Viitanen et al. ............... 435/161 |
| 2011/0117612 A1* | 5/2011 | Yukawa et al. ............... 435/106 |

OTHER PUBLICATIONS

UniProt Accession No. Q6DB06, Dec. 2011, 2 pages.*
Meiswinkel et al., "Accelerated pentose utilization by *Corynebacterium glutamicum* for accelerated production of lysine, glutamate, ornithine and putrescine", Microbial Biotechnol. 6:131-140, available online Nov. 20, 2012.*
Blombach et al., "Carbohydrate metabolism in *Corynebacterium glutamicum* and applications for the metabolic engineering of L-lysine production strains," Appl Microbiol Biotechnol 86:1313-1322 (2010).
Buschke et al., "Metabolic engineering of *Corynebacterium glutamicum* for production of 1,5-diaminopentane from hemicellulose," Biotechnol. J. 6:306-317 (2011).
Sasaki et al., "Simultaneous utilization of D-cellobiose, D-glucose, and D-xylose by recombinant *Corynebacterium glutamicum* under oxygen-deprived conditions," Appl Microbiol Biotechnol 86:691-699 (2008).
Kawaguchi et al., "Engineering of a Xylose Metabolic Pathway in *Corynebacterium glutamicum*," Applied and Environmental Microbiology 72(5):3418-3428 (May 2006).

* cited by examiner

*Primary Examiner* — David J Steadman
(74) *Attorney, Agent, or Firm* — Seed IP Law Group PLLC

(57) ABSTRACT

The present invention relates to microorganisms of *corynebacterium* which can utilize xylose and to a method for producing L-lysine using same. More particularly, the present invention relates to microorganisms of *corynebacterium* which are modified, in which genes encoding xylose isomerase and xylulokinase which are xylose synthases are introduced to express the xylose synthase. The present invention also relates to a method for producing L-lysine, comprising a step of culturing the modified microorganisms of *corynebacterium* using xylose as a carbon source, and recovering L-lysine from the culture.

7 Claims, 2 Drawing Sheets ative embodiments are provided as an example to describe the present invention in more detail. However, the present invention is not limited to these exemplary embodiments.

SEQUENCE LISTING

```
<160> NUMBER OF SEQ ID NOS: 18

<210> SEQ ID NO 1
<211> LENGTH: 439
<212> TYPE: PRT
<213> ORGANISM: Erwinia carotovora
<220> FEATURE:
```

```
<221> NAME/KEY: PEPTIDE
<222> LOCATION: (1)...(439)
<223> OTHER INFORMATION: XylA

<400> SEQUENCE: 1
```

| | | | | | | | | | | | | | | |
|---|---|---|---|---|---|---|---|---|---|---|---|---|---|---|
| Met | Gln | Ala | Tyr | Phe | Glu | Gln | Ile | Glu | Lys | Val | Arg | Tyr | Glu | Gly | Ser |
| 1 | | | | 5 | | | | | 10 | | | | | 15 | |

Gln Ser Ser Asn Pro Phe Ala Phe Arg His Tyr Asn Pro Asp Gln Glu
             20                  25                  30

Ile Leu Gly Lys Arg Met Ala Asp His Leu Arg Phe Ala Val Ala Tyr
             35                  40                  45

Trp His Thr Phe Cys Trp Asn Gly Ser Asp Met Phe Gly Val Gly Ser
 50                  55                  60

Phe Ala Arg Pro Trp Gln Gln Ser Gly Asp Ala Leu Glu Leu Ala Lys
 65                  70                  75                  80

Arg Lys Ala Asp Ile Ala Phe Glu Phe Phe Gln Lys Leu Ser Val Pro
                 85                  90                  95

Tyr Tyr Cys Phe His Asp Val Asp Val Ala Pro Glu Gly Asn Ser Leu
                100                 105                 110

Lys Glu Tyr Leu His Asn Ile Ala Val Ile Thr Asp Val Leu Ala Glu
            115                 120                 125

Lys Gln Gln Asp Ser Gly Val Lys Leu Leu Trp Gly Thr Ala Asn Cys
            130                 135                 140

Phe Thr Asn Pro Arg Tyr Gly Ala Gly Ala Ala Thr Asn Pro Asp Pro
145                 150                 155                 160

Asp Val Phe Ala Trp Ala Ala Thr Gln Val Phe Thr Ala Met Asn Ala
                165                 170                 175

Thr Lys Thr Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
            195                 200                 205

Ile Gly Arg Phe Met Gln Met Val Val Glu His Lys His Lys Ile Gly
            210                 215                 220

Phe Gln Gly Thr Leu Leu Ile Glu Pro Lys Pro Gln Glu Pro Thr Lys
225                 230                 235                 240

His Gln Tyr Asp Tyr Asp Val Ala Thr Val Tyr Gly Phe Leu Lys Gln
                245                 250                 255

Phe Gly Leu Glu Lys Glu Ile Lys Val Asn Val Glu Ala Asn His Ala
            260                 265                 270

Thr Leu Ala Gly His Ser Phe His His Glu Ile Ala Thr Ala Val Ala
            275                 280                 285

Leu Gly Val Phe Gly Ser Val Asp Ala Asn Arg Gly Asp Pro Gln Leu
            290                 295                 300

Gly Trp Asp Thr Asp Gln Phe Pro Asn Ser Val Glu Glu Asn Thr Leu
305                 310                 315                 320

Ile Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Arg Tyr Asp Leu
            340                 345                 350

Phe His Ala His Ile Gly Ala Met Asp Thr Met Ala Leu Ala Leu Lys
            355                 360                 365

Ala Ala Ala Arg Met Ile Glu Asp Asp Lys Leu Asn Gln Leu Val Ala
            370                 375                 380

Lys Arg Tyr Ala Gly Trp Asn Gly Glu Leu Gly Gln Gln Ile Leu Gln

```
                385             390             395             400
Gly Asn Ala Ser Leu Glu Ser Leu Ala Gln Tyr Ala Glu Ser His Gln
                    405             410             415

Leu Ala Pro Gln His Gln Ser Gly Gln Gln Glu Leu Leu Glu Asn Leu
                420             425             430

Val Asn Arg His Leu Phe Gly
                435

<210> SEQ ID NO 2
<211> LENGTH: 485
<212> TYPE: PRT
<213> ORGANISM: Erwinia carotovora
<220> FEATURE:
<221> NAME/KEY: PEPTIDE
<222> LOCATION: (1)...(485)
<223> OTHER INFORMATION: XylB

<400> SEQUENCE: 2

Met Tyr Ile Gly Ile Asp Leu Gly Thr Ser Gly Val Lys Ala Ile Leu
  1               5                  10                  15

Leu Asp Glu Thr Gly Glu Val Ile Ala Ser His Ser Ala Ala Leu Ser
                 20                  25                  30

Ile Ser Arg Pro His Pro Leu Trp Ser Glu Gln Ala Pro Glu Asp Trp
             35                  40                  45

Trp Gln Ala Thr Asp Gln Ala Leu Gln Ala Leu Ala Ala Thr His Ser
         50                  55                  60

Leu Arg Ala Val Lys Ala Leu Gly Leu Thr Gly Gln Met His Gly Ala
 65                  70                  75                  80

Thr Leu Leu Asp Ala His Gln Asn Ile Leu Arg Pro Ala Ile Leu Trp
                     85                  90                  95

Asn Asp Gly Arg Ser Ala Ala Gln Cys Arg Thr Leu Glu Gln Leu Val
                100                 105                 110

Pro Thr Ser Arg Gln Ile Thr Gly Asn Leu Met Met Pro Gly Phe Thr
            115                 120                 125

Ala Pro Lys Leu Lys Trp Val Gln Glu Asn Glu Ser Asp Ile Phe Arg
        130                 135                 140

Gln Ile Asp Lys Val Leu Leu Pro Lys Asp Tyr Leu Arg Trp Arg Leu
145                 150                 155                 160

Thr Gly Glu Phe Ala Ser Asp Met Ser Asp Ala Ala Gly Thr Leu Trp
                165                 170                 175

Leu Asp Val Ala Lys Arg Asp Trp Ser Asp Ala Leu Leu Glu Ala Cys
            180                 185                 190

Ser Leu Ser Arg Glu His Met Pro Thr Leu Tyr Glu Gly Asn Gln Ile
        195                 200                 205

Thr Gly Tyr Leu Arg Pro Asp Ile Ala Ser Arg Trp Gly Met Asp Pro
    210                 215                 220

Val Pro Val Ile Ala Gly Gly Asp Asn Ala Ala Gly Ala Ile Gly
225                 230                 235                 240

Val Gly Leu Tyr Gln Thr Gly Gln Ala Met Leu Ser Leu Gly Thr Ser
                245                 250                 255

Gly Val Tyr Phe Ala Val Ser Asp Gly Phe Leu Ser Asn Pro Gln His
            260                 265                 270

Ala Val His Ser Phe Cys His Ala Leu Pro Asn Thr Trp His Leu Met
        275                 280                 285

Ser Val Met Leu Ser Ala Ala Ser Cys Leu Asp Trp Val Ala Arg Leu
    290                 295                 300
```

```
Thr His Ala Glu Ser Val Pro Ala Leu Leu Gln Glu Val Ala Ser Met
305                 310                 315                 320

Pro Ala Asp Asp Thr Ile Thr Pro Val Trp Phe Leu Pro Tyr Leu Ser
                325                 330                 335

Gly Glu Arg Thr Pro His Asn Asn Pro Asp Ala Lys Gly Ala Phe Trp
            340                 345                 350

Gly Leu Thr His Gln His Gly Arg Ala Glu Leu Ala Lys Ala Val Leu
        355                 360                 365

Glu Gly Val Gly Phe Ala Leu Ala Asp Gly Met Asp Ala Leu His Met
370                 375                 380

Thr Gly Leu Lys Pro Asp Ser Ile Thr Leu Ile Gly Gly Gly Ala Arg
385                 390                 395                 400

Ser Asp Tyr Trp Arg Gln Met Leu Ala Asp Ile Ser Gly Gln Thr Leu
                405                 410                 415

Glu Tyr Arg Thr Gly Gly Asp Val Gly Pro Ala Leu Gly Ala Ala Arg
            420                 425                 430

Leu Ala Gln Ile Ala Met His Pro His Thr Pro Leu Ala Glu Leu Leu
        435                 440                 445

Pro Pro Leu Pro Met Glu Gln Val His Gln Pro Asn Thr Gln Arg His
450                 455                 460

Ala Asp Tyr Ala Glu Arg Arg Arg Thr Phe Lys Thr Leu Tyr Gln Gln
465                 470                 475                 480

Leu Ser Pro Leu Met
                485

<210> SEQ ID NO 3
<211> LENGTH: 1320
<212> TYPE: DNA
<213> ORGANISM: Erwinia carotovora
<220> FEATURE:
<221> NAME/KEY: gene
<222> LOCATION: (1)...(1320)
<223> OTHER INFORMATION: XlyA

<400> SEQUENCE: 3
atgcaagcct attttgaaca gatcgaaaaa gttcgttatg aaggtagcca aagcagtaat      60
cccttcgcct ttcgtcacta caatcccgat caggaaattc tcggtaaacg tatggcggac     120
catttgcgtt ttgccgtcgc ttattggcac acgttctgct ggaacggctc ggatatgttc     180
ggcgtcggat cctttgcccg gccgtggcag cagtcgggcg atgcgctgga actggcgaag     240
cgcaaagcgg atatcgcatt cgaattcttt caaaaactaa gcgtgcctta ctactgcttt     300
catgacgtcg atgtcgcgcc ggaagggaac tcgctgaaag aatatctgca taacattgcg     360
gtgatcaccg atgtgctggc ggaaaagcag caggatagcg gcgtgaagct gctgtggggc     420
accgctaact gcttcaccaa tccccgctat ggcgcaggcg cggccaccaa tcctgatcca     480
gatgtgtttg cctgggctgc tacgcaggtg ttcacggcaa tgaacgcgac caaaacactg     540
ggcggtgaaa actatgtgct gtggggcggg cgcgaagggt atgaaactct gctcaatacc     600
gacctgcgtc aggagcgtga gcaaattggc cgctttatgc aaatggttgt cgagcataaa     660
cacaaaatcg gttttcaggg cacactgctc attgaaccga accgcaggaa ccgactaaa     720 catcagtacg attacgatgt cgccactgtt tatggcttcc tgaaacagtt tgggctggaa     780
aaagagatta aagtcaacgt ggaagccaac cacgcgacgc ttgctgggca ttcattccac     840
catgagatcg ccaccgctgt cgcgctgggc gttttcggat cggtcgatgc caatcgcggc     900
```

```
gaccctcagc ttggctggga caccgatcag ttccctaaca gcgtggaaga aaacacgctg      960
atcatgtatg aaattctcaa ggcaggcggc ttcacgacag gtgggctgaa ctttgatgcc     1020
aaagttcgtc gccagagcac cgatcgctat gaccttttcc atgcgcatat cggcgcgatg     1080
gatacaatgg cactggcgct caaggctgct gccagaatga ttgaagatga taagctcaat     1140
caattggtcg ccaagcgcta tgcgggctgg aacggtgaac taggtcagca aattctgcaa     1200
ggcaacgcgt cgctggaatc gctggctcag tatgcgaaaa gccatcaact ggcaccacag     1260
caccagagcg gccagcagga actgctggaa aatctggtta accgccatct atttggctag     1320
```

<210> SEQ ID NO 4
<211> LENGTH: 1458
<212> TYPE: DNA
<213> ORGANISM: Erwinia carotovora
<220> FEATURE:
<221> NAME/KEY: gene
<222> LOCATION: (1)...(1458)
<223> OTHER INFORMATION: XlyB

<400> SEQUENCE: 4

```
atgtatatcg gtattgatct gggcacttcc ggtgttaaag ccatcttact ggatgaaaca       60
ggagaggtga tcgccagcca tagcgccgcg ctgagcattt ctcgtccgca tccgctttgg      120
tcggagcaag cgcctgagga ctggtggcag gcaacagacc aagcgctaca agcattggca      180
gcaacacaca gccttcgcgc cgtgaaagcg ctggggttga ccgggcaaat gcacggggca      240
accttgctgg acgctcacca gaacattctg cgacctgcga tcctttggaa tgacggacgt      300
agcgcggcgc aatgccgaac gctggaacag ttggtgccta cctcgcgcca gattaccggc      360
aacctgatga tgccgggctt tactgctccc aaactaaaat gggtgcagga aaacgaaagc      420
gatatctttc gccaaatcga caaggtcctg ctgccaaaag actatctccg ctggcgtctg      480 acagggggaat ttgccagcga tatgtccgat gcggctggaa ccctctggct ggacgtcgcc      540
aaacgggatt ggagcgatgc tctgctggaa gcctgctcgc tgagccgtga acacatgccc      600
acgctgtatg aaggcaacca gattaccggt tatctgcgac ctgacatcgc cagtcgctgg      660
ggtatggatc ccgtccccgt tattgctggc ggtggggata acgcagcagg cgcgattggc      720
gtcgggctgt atcaaaccgg tcaggcgatg ctgtctctcg gcacatccgg cgtttatttc      780
gccgtcagcg acggttttct cagtaatcct cagcatgccg tccacagctt ttgccatgcg      840
ctgccaaata cctggcacct gatgtccgtg atgttaagcg cggcgtcctg cctagattgg      900
gtcgcccgcc tgacacacgc cgagagcgtg cccgcactgt gcaggaagt cgcctcaatg      960 ccagccgatg acacgataac gccagtgtgg ttttgcccct atctttctgg cgagcgtaca     1020
ccgcacaaca atcctgatgc caaggcgca ttctgggggc tcacccacca gcacggccgc     1080
gcagagctgg caaaagcggt gctggaaggc gtgggatttg cgcttgccga tgggatggac     1140
gcactgcata tgactgggct aaaacccgat agcatcacgc taattggcgg tggcgcacgt     1200
agcgactatt ggcggcaaat gttggcagat atcagtggtc aaactctgga ataccgcacg     1260
ggcggcgatg tcggcccagc gctgggtgcc gcccgtctgg cacaaatcgc tatgcatccc     1320
catacgccac tggcagaact cttgccgccg ctaccgatgg agcaggttca tcagccgaat     1380
acccagcgcc acgccgacta tgccgagcgt aggcgcacat ttaaaacgct ctaccaacag     1440
cttagtccgc tgatgtag                                                  1458
```

<210> SEQ ID NO 5
<211> LENGTH: 30

```
<212> TYPE: DNA
<213> ORGANISM: Artificial Sequence
<220> FEATURE:
<223> OTHER INFORMATION: xylAB(Er) primer

<400> SEQUENCE: 5
acacatatgc aagcctattt tgaacagatc                                              30

<210> SEQ ID NO 6
<211> LENGTH: 30
<212> TYPE: DNA
<213> ORGANISM: Artificial Sequence
<220> FEATURE:
<223> OTHER INFORMATION: xylAB(Er) primer

<400> SEQUENCE: 6
agaactagtg cctttggtg gtgtttaagt                                               30

<210> SEQ ID NO 7
<211> LENGTH: 36
<212> TYPE: DNA
<213> ORGANISM: Artificial Sequence
<220> FEATURE:
<223> OTHER INFORMATION: pcj7-xylAB(Er) primer

<400> SEQUENCE: 7
gagttcctcg agactagtag aaacatccca gcgcta                                       36

<210> SEQ ID NO 8
<211> LENGTH: 36
<212> TYPE: DNA
<213> ORGANISM: Artificial Sequence
<220> FEATURE:
<223> OTHER INFORMATION: pcj7-xylAB(Er) primer

<400> SEQUENCE: 8
gatgtcgggc ccactaggcc tttttggtgg tgttta                                       36

<210> SEQ ID NO 9
<211> LENGTH: 3440
<212> TYPE: DNA
<213> ORGANISM: Artificial Sequence
<220> FEATURE:
<223> OTHER INFORMATION: gene fragment pcj7-xylAB(Er)

<400> SEQUENCE: 9
agaaacatcc cagcgctact aatagggagc gttgaccttc cttccacgga ccggtaatcg              60
gagtgcctaa aaccgcatgc ggcttaggct ccaagatagg ttctgcgcgg ccgggtaatg             120
catcttcttt agcaacaagt tgaggggtag gtgcaaataa gaacgacata gaaatcgtct             180
cctttctgtt tttaatcaac atacaccacc acctaaaaat tccccgacca gcaagttcac             240
agtattcggg cacaatatcg ttgccaaaat attgtttcgg aatatcatgg gatacgtacc             300
caacgaaagg aaacacatat gcaagcctat tttgaacaga tcgaaaaagt tcgttatgaa             360
ggtagccaaa gcagtaatcc cttcgccttt cgtcactaca tcccgatca ggaaattctc              420 ggtaaacgta tggcggacca tttgcgtttt gccgtcgctt attggcacac gttctgctgg             480
aacggctcgg atatgttcgg cgtcggatcc tttgcccggc cgtggcagca gtcgggcgat             540
gcgctggaac tggcgaagcg caaagcggat atcgcattcg aattctttca aaaactaagc             600
gtgccttact actgctttca tgacgtcgat gtcgcgccgg aagggaactc gctgaaagaa             660
tatctgcata acattgcggt gatcaccgat gtgctggcgg aaaagcagca ggatagcggc             720
```

```
gtgaagctgc tgtggggcac cgctaactgc ttcaccaatc cccgctatgg cgcaggcgcg      780
gccaccaatc ctgatccaga tgtgtttgcc tgggctgcta cgcaggtgtt cacggcaatg      840
aacgcgacca aaacactggg cggtgaaaac tatgtgctgt ggggcgggcg cgaagggtat      900
gaaactctgc tcaataccga cctgcgtcag gagcgtgagc aaattggccg ctttatgcaa      960
atggttgtcg agcataaaca caaaatcggt tttcagggca cactgctcat tgaaccgaaa     1020
ccgcaggaac cgactaaaca tcagtacgat tacgatgtcg ccactgttta tggcttcctg     1080
aaacagtttg gctggaaaaa agagattaaa gtcaacgtgg aagccaacca cgcgacgctt     1140
gctgggcatt cattccacca tgagatcgcc accgctgtcg cgctgggcgt tttcggatcg     1200
gtcgatgcca atcgcggcga ccctcagctt ggctgggaca ccgatcagtt ccctaacagc     1260
gtggaagaaa acacgctgat catgtatgaa attctcaagg caggcggctt cacgacaggt     1320
gggctgaact ttgatgccaa agttcgtcgc cagagcaccg atcgctatga ccttttccat     1380
gcgcatatcg gcgcgatgga tacaatggca ctggcgctca aggctgctgc cagaatgatt     1440
gaagatgata agctcaatca attggtcgcc aagcgctatg cgggctggaa cggtgaacta     1500
ggtcagcaaa ttctgcaagg caacgcgtcg ctggaatcgc tggctcagta tgcggaaagc     1560
catcaactgg caccacagca ccagagcggc cagcaggaac tgctggaaaa tctggttaac     1620
cgccatctat ttggctagtg cggtacgctt gcctgctacg gcaggttaaa aaactgccgt     1680
agcataaggt tatcaggagc gactatgtat atcggtattg atctgggcac ttccggtgtt     1740
aaagccatct tactggatga aacaggagag gtgatcgcca ccatagcgc cgcgctgagc     1800 atttctcgtc cgcatccgct ttggtcgag caagcgcctg aggactggtg gcaggcaaca     1860
gaccaagcgc tacaagcatt ggcagcaaca cacagccttc gcgccgtgaa agcgctgggg     1920
ttgaccgggc aaatgcacgg ggcaaccttg ctggacgctc accagaacat tctgcgacct     1980
gcgatccttt ggaatgacgg acgtagcgcg gcgcaatgcc gaacgctgga acagttggtg     2040
cctacctcgc gccagattac cggcaacctg atgatgccgg gctttactgc tcccaaacta     2100
aaatgggtgc aggaaaacga aagcgatatc tttcgccaaa tcgacaaggt cctgctgcca     2160
aaagactatc tccgctggcg tctgacaggg gaatttgcca gcgatatgtc cgatgcggct     2220
ggaaccctct ggctggacgt cgccaaacgg gattggagcg atgctctgct ggaagcctgc     2280
tcgctgagcc gtgaacacat gcccacgctg tatgaaggca accagattac cggttatctg     2340
cgacctgaca tcgccagtcg ctgggggtatg gatcccgtcc ccgttattgc tggcggtggg     2400
gataacgcag caggcgcgat tggcgtcggg ctgtatcaaa ccggtcaggc gatgctgtct     2460
ctcggcacat ccggcgttta tttcgccgtc agcgacggtt ttctcagtaa tcctcagcat     2520
gccgtccaca gcttttgcca tgcgctgcca aatacctggc acctgatgtc cgtgatgtta     2580
agcgcggcgt cctgcctaga ttgggtcgcc cgcctgacac acgccgagag cgtgcccgca     2640
ctgttgcagg aagtcgcctc aatgccagcc gatgacacga taacgccagt gtggttttg     2700 ccctatcttt ctggcgagcg tacaccgcac aacaatcctg atgccaaagg cgcattctgg     2760
gggctcaccc accagcacgg ccgcgcagag ctggcaaaag cggtgctgga aggcgtggga     2820
tttgcgcttg ccgatgggat ggacgcactg catatgactg gctaaaacc cgatagcatc     2880 acgctaattg gcggtggcgc acgtagcgac tattggcggc aaatgttggc agatatcagt     2940
ggtcaaactc tggaataccg cacgggcggg gatgtcggcc cagcgctggg tgccgcccgt     3000
ctggcacaaa tcgctatgca tcccatacg ccactggcga aactcttgcc gccgctaccg     3060
atggagcagg ttcatcagcc gaatacccag cgccacgccg actatgccga gcgtaggcgc     3120
```

```
acatttaaaa cgctctacca acagcttagt ccgctgatgt agcaccgttc gtccggtaca    3180
ccggacgggt agtcaactca cccagcgccg cacatcaatc ttctgtaaag ccatcgaaag    3240
cagcaggctg gccgccagcg cgatggtgaa gacatagaag atatcgagaa ccggatgatc    3300
cggcagcatc acatcatgcg tacgtagata gtgaatgatc aacgcgtgga aaccgtaaat    3360
cgccagcgaa tgacgcgaaa tggtggcaaa acccggtaag atccgctggc taaagtagta    3420
cttaaacacc accaaaaggc                                                3440

<210> SEQ ID NO 10
<211> LENGTH: 35
<212> TYPE: DNA
<213> ORGANISM: Artificial Sequence
<220> FEATURE:
<223> OTHER INFORMATION: pcj7 primer

<400> SEQUENCE: 10
tcaaaatagg cttgcatgag tgtttccttt cgttg                                35

<210> SEQ ID NO 11
<211> LENGTH: 34
<212> TYPE: DNA
<213> ORGANISM: Artificial Sequence
<220> FEATURE:
<223> OTHER INFORMATION: xylAB(Ec) primer

<400> SEQUENCE: 11
caacgaaagg aaacacatgc aagcctattt tgac                                 34

<210> SEQ ID NO 12
<211> LENGTH: 36
<212> TYPE: DNA
<213> ORGANISM: Artificial Sequence
<220> FEATURE:
<223> OTHER INFORMATION: xylAB(Ec) primer

<400> SEQUENCE: 12
gatgtcgggc ccactagtgc tgtcattaac acgcca                               36

<210> SEQ ID NO 13
<211> LENGTH: 3145
<212> TYPE: DNA
<213> ORGANISM: Artificial Sequence
<220> FEATURE:
<223> OTHER INFORMATION: gene fragment xylAB(Ec)

<400> SEQUENCE: 13
atgcaagcct attttgacca gctcgatcgc gttcgttatg aaggctcaaa atcctcaaac     60
ccgttagcat tccgtcacta caatcccgac gaactggtgt gggtaagcg tatggaagag    120 cacttgcgtt ttgccgcctg ctactggcac accttctgct ggaacggggc ggatatgttt    180
ggtgtggggg cgtttaatcg tccgtggcag cagcctggtg aggcactggc gttggcgaag    240
cgtaaagcag atgtcgcatt tgagtttttc cacaagttac atgtgccatt ttattgcttc    300
cacgatgtgg atgtttcccc tgagggcgcg tcgttaaaag agtacatcaa taattttgcg    360
caaatggttg atgtcctggc aggcaagcaa gaagagagcg gcgtgaagct gctgtgggga    420
acggccaact gctttacaaa ccctcgctac ggcgcgggtg cggcgacgaa cccagatcct    480
gaagtcttca gctgggcggc aacgcaagtt gttacagcga tggaagcaac ccataaattg    540
ggcggtgaaa actatgtcct gtggggcggt cgtgaaggtt acgaaacgct gttaaatacc    600
```

```
gacttgcgtc aggagcgtga acaactgggc cgctttatgc agatggtggt tgagcataaa    660
cataaaatcg gtttccaggg cacgttgctt atcgaaccga aaccgcaaga accgaccaaa    720
catcaatatg attacgatgc cgcgacggtc tatggcttcc tgaaacagtt tggtctggaa    780
aaagagatta aactgaacat tgaagctaac cacgcgacgc tggcaggtca ctctttccat    840
catgaaatag ccaccgccat tgcgcttggc ctgttcggtt ctgtcgacgc caaccgtggc    900
gatgcgcaac tgggctggga caccgaccag ttcccgaaca gtgtggaaga gaatgcgctg    960
gtgatgtatg aaattctcaa agcaggcggt ttcaccaccg gtggtctgaa cttcgatgcc   1020
aaagtacgtc gtcaaagtac tgataaatat gatctgtttt acggtcatat cggcgcgatg   1080
gatacgatgg cactggcgct gaaaattgca gcgcgcatga ttgaagatgg cgagctggat   1140
aaacgcatcg cgcagcgtta ttccggctgg aatagcgaat tgggccagca aatcctgaaa   1200
ggccaaatgt cactggcaga tttagccaaa tatgctcagg aacatcattt gtctccggtg   1260
catcagagtg gtcgccagga caactggaaa atctggtaa accattatct gttcgacaaa   1320
taacggctaa ctgtgcagtc cgttggcccg gttatcggta gcgataccgg gcattttttt   1380
aaggaacgat cgatatgtat atcgggatag atcttggcac ctcgggcgta aaagttattt   1440
tgctcaacga gcagggtgag gtggttgctg cgcaaacgaa aaagctgacc gtttcgcgcc   1500
cgcatccact ctggtcggaa caagacccgg aacagtggtg gcaggcaact gatcgcgcaa   1560
tgaaagctct gggcgatcag cattctctgc aggacgttaa agcattgggt attgccggcc   1620
agatgcacgg agcaaccttg ctggatgctc agcaacgggt gttacgccct gccattttgt   1680
ggaacgacgg cgcgctgtgcg caagagtgca ctttgctgga agcgcgagtt ccgcaatcgc   1740
gggtgattac cggcaacctg atgatgcccg gatttactgc gcctaaattg ctatgggttc   1800
agcggcatga gccggagata ttccgtcaaa tcgacaaagt attattaccg aaagattact   1860
tgcgtctgcg tatgacgggg gagtttgcca gcgatatgtc tgacgcagct ggcaccatgt   1920
ggctggatgt cgcaaagcgt gactggagtg acgtcatgct gcaggcttgc gacttatctc   1980
gtgaccagat gcccgcatta tacgaaggca gcgaaattac tggtgctttg ttacctgaag   2040
ttgcgaaagc gtggggtatg cgacggtgc cagttgtcgc aggcggtggc gacaatgcag   2100
ctggtgcagt tggtgtggga atggttgatg ctaatcaggc aatgttatcg ctggggacgt   2160
cgggggtcta ttttgctgtc agcgaagggt tcttaagcaa gccagaaagc gccgtacata   2220
gcttttgcca tgcgctaccg caacgttggc atttaatgtc tgtgatgctg agtgcagcgt   2280
cgtgtctgga ttgggccgcg aaattaaccg gcctgagcaa tgtcccagct ttaatcgctg   2340
cagctcaaca ggctgatgaa agtgccgagc cagtttggtt tctgccttat ctttccggcg   2400
agcgtacgcc acacaataat ccccaggcga agggggtttt ctttggtttg actcatcaac   2460
atggccccaa tgaactggcg cgagcagtgc tggaaggcgt gggttatgcg ctggcagatg   2520
gcatggatgt cgtgcatgcc tgcggtatta aaccgcaaag tgttacgttg attggggcg    2580
gggcgcgtag tgagtactgg cgtcagatgc tggcggatat cagcgtcag cagctcgatt   2640
accgtacggg gggggatgtg gggccagcac tgggcgcagc aaggctggcg cagatcgcgg   2700
cgaatccaga gaaatcgctc attgaattgt gccgcaact accgttagaa cagtcgcatc   2760
taccagatgc gcagcgttat gccgcttatc agccacgacg agaaacgttc cgtcgcctct   2820
atcagcaact tctgccatta atggcgtaaa cgttatcccc tgcctgaccg ggtggggat    2880
aattcacatc tatatatctc agtaattaat taatatttag tatgaattta ttctgaaaat   2940
catttgttaa tggcattttt cagttttgtc tttcgttggt tactcgtaat gtatcgctgg   3000
```

```
tagatatgga gatcgttatg aaaacctcaa agactgtggc aaaactatta tttgttgtcg    3060
gggcgctggt ttatctggtt gggctatgga tctcatgccc attgttaagt ggaaaaggct    3120
attttcttgg cgtgttaatg acagc                                         3145

<210> SEQ ID NO 14
<211> LENGTH: 318
<212> TYPE: DNA
<213> ORGANISM: Artificial Sequence
<220> FEATURE:
<223> OTHER INFORMATION: pcj7 promoter sequence

<400> SEQUENCE: 14
agaaacatcc cagcgctact aatagggagc gttgaccttc cttccacgga ccggtaatcg     60
gagtgcctaa aaccgcatgc ggcttaggct ccaagatagg ttctgcgcgg ccgggtaatg    120
catcttcttt agcaacaagt tgaggggtag gtgcaaataa gaacgacata gaaatcgtct    180
cctttctgtt tttaatcaac atacaccacc acctaaaaat tccccgacca gcaagttcac    240
agtattcggg cacaatatcg ttgccaaaat attgtttcgg aatatcatgg gatacgtacc    300
caacgaaagg aaacacat                                                  318

<210> SEQ ID NO 15
<211> LENGTH: 23
<212> TYPE: DNA
<213> ORGANISM: Artificial Sequence
<220> FEATURE:
<223> OTHER INFORMATION: pcj7 primer

<400> SEQUENCE: 15
aatctagaaa catcccagcg cta                                             23

<210> SEQ ID NO 16
<211> LENGTH: 29
<212> TYPE: DNA
<213> ORGANISM: Artificial Sequence
<220> FEATURE:
<223> OTHER INFORMATION: pcj7 primer

<400> SEQUENCE: 16
aaactagtca tatgtgtttc ctttcgttg                                       29

<210> SEQ ID NO 17
<211> LENGTH: 2844
<212> TYPE: DNA
<213> ORGANISM: Artificial Sequence
<220> FEATURE:
<223> OTHER INFORMATION: gene fragment xylAB(Er)

<400> SEQUENCE: 17
atgcaagcct attttgaaca gatcgaaaaa gttcgttatg aaggtagcca aagcagtaat     60
cccttcgcct ttcgtcacta caatcccgat caggaaattc tcggtaaacg tatggcggac    120
catttgcgtt ttgccgtcgc ttattggcac acgttctgct ggaacggctc ggatatgttc    180
ggcgtcggat cctttgcccg gccgtggcag cagtcgggcg atgcgctgga actggcgaag    240
cgcaaagcgg atatcgcatt cgaattcttt caaaaactaa gcgtgcctta ctactgcttt    300
catgacgtcg atgtcgcgcc ggaagggaac tcgctgaaag aatatctgca taacattgcg    360
gtgatcaccg atgtgctggc ggaaaagcag caggatagcg gcgtgaagct gctgtggggc    420
accgctaact gcttcaccaa tccccgctat ggcgcaggcg cggccaccaa tcctgatcca    480
```

-continued

```
gatgtgtttg cctgggctgc tacgcaggtg ttcacggcaa tgaacgcgac caaaacactg    540
ggcggtgaaa actatgtgct gtggggcggg cgcgaagggt atgaaactct gctcaatacc    600
gacctgcgtc aggagcgtga gcaaattggc cgctttatgc aaatggttgt cgagcataaa    660
cacaaaatcg gttttcaggg cacactgctc attgaaccga aaccgcagga accgactaaa    720
catcagtacg attacgatgt cgccactgtt tatggcttcc tgaaacagtt tgggctggaa    780
aaagagatta aagtcaacgt ggaagccaac cacgcgacgc ttgctgggca ttcattccac    840
catgagatcg ccaccgctgt cgcgctgggc gttttcggat cggtcgatgc caatcgcggc    900
gaccctcagc ttggctggga caccgatcag ttccctaaca gcgtggaaga aaacacgctg    960
atcatgtatg aaattctcaa ggcaggcggc ttcacgacag gtgggctgaa ctttgatgcc   1020
aaagttcgtc gccagagcac cgatcgctat gaccttttcc atgcgcatat cggcgcgatg   1080
gatacaatgg cactggcgct caaggctgct gccagaatga ttgaagatga taagctcaat   1140
caattggtcg ccaagcgcta tgcgggctgg aacggtgaac taggtcagca aattctgcaa   1200
ggcaacgcgt cgctggaatc gctggctcag tatgcgaaaa gccatcaact ggcaccacag   1260
caccagagcg gccagcagga actgctggaa aatctggtta accgccatct atttggctag   1320
tgcggtacgc ttgcctgcta cggcaggtta aaaaactgcc gtagcataag gttatcagga   1380
gcgactatgt atatcggtat tgatctgggc acttccggtg ttaaagccat cttactggat   1440
gaaacaggag aggtgatcgc cagccatagc gccgcgctga gcatttctcg tccgcatccg   1500
ctttggtcgg agcaagcgcc tgaggactgg tggcaggcaa cagaccaagc gctacaagca   1560
ttggcagcaa cacacagcct tcgcgccgtg aaagcgctgg ggttgaccgg gcaaatgcac   1620
ggggcaacct tgctggacgc tcaccagaac attctgcgac ctgcgatcct ttggaatgac   1680
ggacgtagcg cggcgcaatg ccgaacgctg gaacagttgg tgcctacctc gcgccagatt   1740
accggcaacc tgatgatgcc gggctttact gctcccaaac taaaatgggt gcaggaaaac   1800
gaaagcgata tctttcgcca aatcgacaag gtcctgctgc aaaagactac tctccgctgg   1860
cgtctgacag gggaatttgc cagcgatatg tccgatgcgg ctggaaccct ctggctggac   1920
gtcgccaaac gggattggag cgatgctctg ctggaagcct gctcgctgag ccgtgaacac   1980
atgcccacgc tgtatgaagg caaccagatt accggttatc tgcgacctga catcgccagt   2040
cgctggggta tggatcccgt ccccgttatt gctggcggtg gggataacgc agcaggcgcg   2100
attggcgtcg ggctgtatca aaccggtcag gcgatgctgt ctctcggcac atccggcgtt   2160
tatttcgccg tcagcgacgg ttttctcagt aatcctcagc atgccgtcca cagcttttgc   2220
catcgcctgc caaataccctg gcacctgatg tccgtgatgt taagcgcggc gtcctgccta   2280
gattgggtcg cccgcctgac acacgccgag agcgtgcccg cactgttgca ggaagtcgcc   2340
tcaatgccag ccgatgacac gataacgcca gtgtggtttt tgccctatct ttctggcgag   2400
cgtacaccgc acaacaatcc tgatgccaaa ggcgcattct gggggctcac ccaccagcac   2460
ggccgcgcag agctggcaaa agcggtgctg gaaggcgtgg gatttgcgct tgccgatggg   2520
atggacgcac tgcatatgac tgggctaaaa cccgatagca tcacgctaat tggcggtggc   2580
gcacgtagcg actattggcg gcaaatgttg cagatatca gtggtcaaac tctggaatac   2640
cgcacgggcg gcgatgtcgg cccagcgctg gtgccgccc gtctggcaca aatcgctatg   2700
catccccata cgccactggc agaactcttg ccgccgctac cgatggagca ggttcatcag   2760
ccgaatacc agcgccacgc cgactatgcc gagcgtaggc gcacatttaa aacgctctac   2820
caacagctta gtccgctgat gtag                                          2844
```

<210> SEQ ID NO 18
<211> LENGTH: 3122
<212> TYPE: DNA
<213> ORGANISM: Artificial Sequence
<220> FEATURE:
<223> OTHER INFORMATION: xylAB(Er) fragment

<400> SEQUENCE: 18

| | | | | | |
|---|---|---|---|---|---|
| atgcaagcct | attttgaaca | gatcgaaaaa | gttcgttatg | aaggtagcca | aagcagtaat | 60 |
| cccttcgcct | tcgtcacta | caatcccgat | caggaaattc | tcggtaaacg | tatggcggac | 120 |
| catttgcgtt | ttgccgtcgc | ttattggcac | acgttctgct | ggaacggctc | ggatatgttc | 180 |
| ggcgtcggat | cctttgcccg | gccgtggcag | cagtcgggcg | atgcgctgga | actggcgaag | 240 |
| cgcaaagcgg | atatcgcatt | cgaattcttt | caaaaactaa | gcgtgcctta | ctactgcttt | 300 |
| catgacgtcg | atgtcgcgcc | ggaagggaac | tcgctgaaag | aatatctgca | taacattgcg | 360 |
| gtgatcaccg | atgtgctggc | ggaaaagcag | caggatagcg | gcgtgaagct | gctgtggggc | 420 |
| accgctaact | gcttcaccaa | tccccgctat | ggcgcaggcg | cggccaccaa | tcctgatcca | 480 |
| gatgtgtttg | cctgggctgc | tacgcaggtg | ttcacggcaa | tgaacgcgac | caaaacactg | 540 |
| ggcggtgaaa | actatgtgct | gtggggcggg | cgcgaagggt | atgaaactct | gctcaatacc | 600 |
| gacctgcgtc | aggagcgtga | gcaaattggc | cgctttatgc | aaatggttgt | cgagcataaa | 660 |
| cacaaaatcg | ttttcagggc | acactgctc | attgaaccga | accgcagga | accgactaaa | 720 |
| catcagtacg | attacgatgt | cgccactgtt | tatggcttcc | tgaaacagtt | tgggctggaa | 780 |
| aaagagatta | agtcaacgt | ggaagccaac | cacgcgacgc | ttgctgggca | ttcattccac | 840 |
| catgagatcg | ccaccgctgt | cgcgctgggc | gttttcggat | cggtcgatgc | caatcgcggc | 900 |
| gaccctcagc | ttggctggga | caccgatcag | ttccctaaca | gcgtggaaga | aaacacgctg | 960 |
| atcatgtatg | aaattctcaa | ggcaggcggc | ttcacgacag | gtgggctgaa | ctttgatgcc | 1020 |
| aaagttcgtc | gccagagcac | cgatcgctat | gaccttttcc | atgcgcatat | cggcgcgatg | 1080 |
| gatacaatgg | cactggcgct | caaggctgct | gccagaatga | ttgaagatga | taagctcaat | 1140 |
| caattggtcg | ccaagcgcta | tgcgggctgg | aacggtgaac | taggtcagca | aattctgcaa | 1200 |
| ggcaacgcgt | cgctggaatc | gctggctcag | tatgcggaaa | gccatcaact | ggcaccacag | 1260 |
| caccagagcg | gccagcagga | actgctgaaa | atctggtta | accgccatct | atttggctag | 1320 |
| tgcggtacgc | ttgcctgcta | cggcaggtta | aaaaactgcc | gtagcataag | gttatcagga | 1380 |
| gcgactatgt | atatcggtat | tgatctgggc | acttccggtg | ttaaagccat | cttactggat | 1440 |
| gaaacaggag | aggtgatcgc | cagccatagc | gccgcgctga | gcatttctcg | tccgcatccg | 1500 |
| ctttggtcgg | agcaagcgcc | tgaggactgg | tggcaggcaa | cagaccaagc | gctacaagca | 1560 |
| ttggcagcaa | cacacagcct | tcgcgccgtg | aaagcgctgg | ggttgaccgg | caaatgcac | 1620 |
| ggggcaacct | gctgacgcc | tcaccagaac | attctgcgac | ctgcgatcct | ttggaatgac | 1680 |
| ggacgtagcg | cggcgcaatg | ccgaacgctg | gaacagttgg | tgcctacctc | gcgccagatt | 1740 |
| accggcaacc | tgatgatgcc | gggctttact | gctcccaaac | taaatgggt | gcaggaaaac | 1800 |
| gaaagcgata | tctttcgcca | aatcgacaag | gtcctgctgc | caaagacta | tctccgctgg | 1860 |
| cgtctgacag | gggaatttgc | cagcgatatg | tccgatgcgg | ctggaacccct | ctggctggac | 1920 |
| gtcgccaaac | gggattggag | cgatgctctg | ctggaagcct | gctcgctgag | ccgtgaacac | 1980 |
| atgcccacgc | tgtatgaagg | caaccagatt | accggttatc | tgcgacctga | catcgccagt | 2040 |

-continued

```
cgctggggta tggatcccgt ccccgttatt gctggcggtg gggataacgc agcaggcgcg    2100
attggcgtcg ggctgtatca aaccggtcag gcgatgctgt ctctcggcac atccggcgtt    2160
tatttcgccg tcagcgacgg ttttctcagt aatcctcagc atgccgtcca cagcttttgc    2220
catgcgctgc caaatacctg gcacctgatg tccgtgatgt taagcgcggc gtcctgccta    2280
gattgggtcg cccgcctgac acacgccgag agcgtgcccg cactgttgca ggaagtcgcc    2340
tcaatgccag ccgatgacac gataacgcca gtgtggtttt tgccctatct ttctggcgag    2400
cgtacaccgc acaacaatcc tgatgccaaa ggcgcattct gggggctcac ccaccagcac    2460
ggccgcgcag agctggcaaa agcggtgctg gaaggcgtgg gatttgcgct tgccgatggg    2520
atggacgcac tgcatatgac tgggctaaaa cccgatagca tcacgctaat tggcggtggc    2580
gcacgtagcg actattggcg gcaaatgttg gcagatatca gtggtcaaac tctggaatac    2640
cgcacgggcg gcgatgtcgg cccagcgctg ggtgccgccc gtctggcaca aatcgctatg    2700
catccccata cgccactggc agaactcttg ccgccgctac cgatggagca ggttcatcag    2760
ccgaataccc agcgccacgc cgactatgcc gagcgtaggc gcacatttaa aacgctctac    2820
caacagctta gtccgctgat gtagcaccgt tcgtccggta caccggacgg gtagtcaact    2880
cacccagcgc cgcacatcaa tcttctgtaa agccatcgaa agcagcaggc tggccgccag    2940
cgcgatggtg aagacataga agatatcgag aaccggatga tccggcagca tcacatcatg    3000
cgtacgtaga tagtgaatga tcaacgcgtg gaaaccgtaa atcgccagcg aatgacgcga    3060
aatggtggca aaacccggta agatccgctg gctaaagtag tacttaaaca ccaccaaaag    3120
gc                                                                   3122
```

MICROORGANISMS OF *CORYNEBACTERIUM* WHICH CAN UTILIZE XYLOSE AND METHOD FOR PRODUCING L-LYSINE USING SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_425_USPC_SEQUENCE_LISTING.txt. The text file is 29.5 KB, was created on Jul. 9, 2014, and is being submitted electronically via EFS-Web.

BACKGROUND OF THE INVENTION

1. Field of the Invention

The present invention relates to a *Corynebacterium* sp. microorganism modified to utilize xylose and a method for producing L-lysine using the same.

2. Description of the Related Art

Industrial microorganisms utilize sugar such as glucose, fructose, and sucrose as a carbon source. Agricultural products are usually used as feedstock to obtain these carbon sources, but they are expensive and are more valuable as food. Recently, instead of using agricultural products as traditional feedstock, cellulosic biomass including agricultural waste or woody waste, industrial waste, etc. has attracted attention as an ideal sugar raw material for fermentation, because it has the advantages of low cost and abundant supply.

Among them, xylose is the second most abundant lignocellulosic carbohydrate in nature, and is a representative cellulosic biomass. Useful materials have been produced from xylose using industrial microorganisms. For example, a method of producing L-amino acid is known, by culturing a *Escherichia* sp. strain in a medium containing a mixture of pentoses including glucose and xylose, wherein the stain is modified to increase expression of xylABFGHR gene cluster encoding an enzyme (xylosidase) hydrolyzing xyloside, which is a glycoside derived from xylose, and then recovering L-amino acid from the medium (Japanese Patent No. 4665567).

On the other hand, a Coryneform bacteria, *Corynebacterium glutamicum*, is known as a Gram-positive strain used in production of various L-amino acids. As described above, because xylose is the second most abundant lignocellulosic carbohydrate in nature, it is expected that L-amino acids such as L-lysine can be more economically produced from *Corynebacterium glutamicum* by using xylose. However, *Corynebacterium glutamicum* does not have important genes which are involved in the metabolic pathway of xylose, which is a pentose, and thus there is a problem that L-amino acid cannot be produced from *Corynebacterium glutamicum* by using xylose. To solve this problem, there has been a report that *Corynebacterium glutamicum* is modified to be able to utilize xylose by introducing xylose isomerase (XylA) and xylulokinase (XylB) derived from *Escherichia coli* (Kawaguchi et al., AEM 72:3418-3428, 2006).

The present inventors have made extensive efforts to produce L-amino acid in a more economical manner, and as a result, they found that when XylA and XylB-encoding genes derived from *Erwinia carotovora* are introduced into *Corynebacterium glutamicum*, the variant is able to utilize xylose to produce L-lysine and also shows more improved xylose-utilizing ability than the previously known Coryneform microorganism introduced with xylA and xylB derived from *Escherichia coli*, thereby completing the present invention.

SUMMARY OF THE INVENTION

An object of the present invention is to provide a modified *Corynebacterium* sp. microorganism able to produce L-lysine by utilizing xylose.

Another object of the present invention is to provide a method for producing L-lysine using the modified *Corynebacterium* sp. microorganism.

DETAILED DESCRIPTION OF THE PREFERRED EMBODIMENTS

Figure 1:
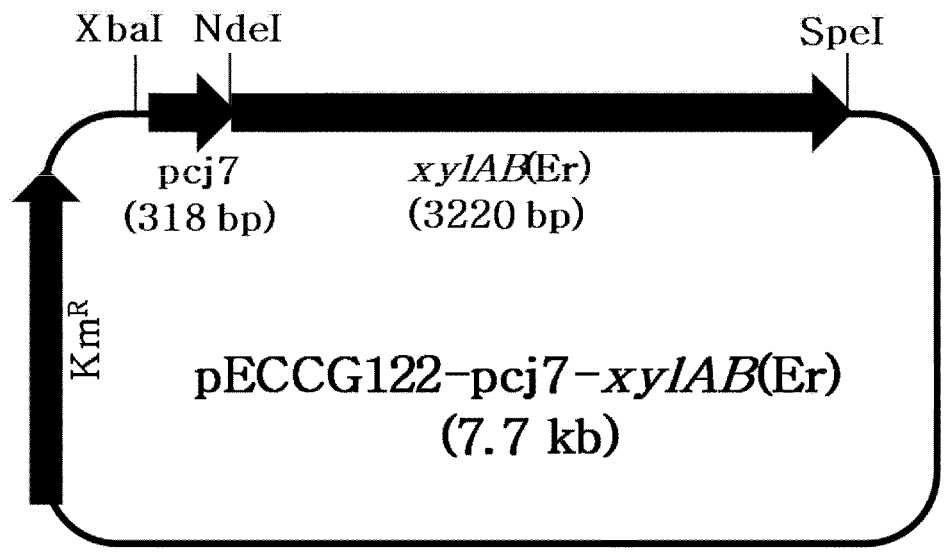
FIG. 1 shows a cleavage map of an expression vector pECCG122-pcj7-xylAB(Er) of the present invention.

In one aspect, the present invention provides a modified *Corynebacterium* sp. microorganism able to produce L-lysine by utilizing xylose, characterized in that activities of xylose isomerase and xylulokinase derived from *Erwinia carotovora* are introduced thereinto.

As used herein, the term "xylose isomerase (XylA)" means an enzyme catalyzing an isomerization reaction from xylose to xylulose, which is involved in the xylose metabolic pathway, and with respect to the object of the present invention, it may be an enzyme derived from *Erwinia carotovora*.

The XylA is xylose isomerase derived from *Erwinia carotovora*, and may include a sequence capable of providing a xylose-utilizing ability by introducing its activity together with activity of xylulokinase derived from *Erwinia carotovora* into the *Corynebacterium* sp. microorganism having no xylose isomerase activity, without limitation. In addition, it is apparent that any sequence having an activity equivalent to that of the above sequence, although it is not derived from *Erwinia carotovora*, is included in the scope of the present invention.

For example, an amino acid sequence of SEQ ID NO: 1, or an amino acid sequence containing a conserved sequence of the amino acid sequence of SEQ ID NO: 1 and substitution, deletion, insertion, addition or inversion of one amino acid or several amino acids (may vary depending on positions and types of amino acid residues in the three-dimensional structure of the protein, specifically 2 to 20, specifically 2 to 10, more specifically 2 to 5 amino acids) at one or more positions, may be included. As long as it is able to maintain or enhance the XylA activity, an amino acid sequence having 80% or more, specifically 90% or more, more specifically 95% or more, much more specifically 97% or more homology with the amino acid sequence of SEQ ID NO: 1 may be included, and the substitution, deletion, insertion, addition or inversion of the amino acid also includes a mutated sequence naturally occurring in the microorganism having XylA activity or an artificially modified sequence.

As used herein, the term "homology" refers to identity between two different amino acid sequences or two different nucleotide sequences, and can be determined by a method well known to those skilled in the art, for example, BLAST 2.0, which calculates parameters such as score, identity, and similarity, but is not particularly limited thereto.

As used herein, the term "xylulokinase" means an enzyme catalyzing a production reaction from xylulose to xylulose 5-phosphate, which is involved in the xylose metabolic pathway, and with respect to the object of the present invention, it may be an enzyme derived from *Erwinia carotovora*.

The XylB is xylulokinase derived from *Erwinia carotovora*, and may include a sequence capable of providing a xylose-utilizing ability by introducing its activity together with activity of xylose isomerase derived from *Erwinia carotovora* into the *Corynebacterium* sp. microorganism having no xylulokinase activity, without limitation. In addition, it is apparent that any sequence having an activity equivalent to that of the above sequence, although it is not derived from *Erwinia carotovora*, is included in the scope of the present invention.

For example, an amino acid sequence of SEQ ID NO: 2, or an amino acid sequence containing a conserved sequence of the amino acid sequence of SEQ ID NO: 2 and substitution, deletion, insertion, addition or inversion of one amino acid or several amino acids (may vary depending on positions and types of amino acid residues in the three-dimensional structure of the protein, specifically 2 to 20, specifically 2 to 10, more specifically 2 to 5 amino acids) at one or more positions, may be included. As long as it is able to maintain or enhance the XylB activity, an amino acid sequence having 80% or more, specifically 90% or more, more specifically 95% or more, much more specifically 97% or more homology with the amino acid sequence of SEQ ID NO: 2 may be included, and the substitution, deletion, insertion, addition or inversion of the amino acid also includes a mutated sequence naturally occurring in the microorganism having XylB activity or an artificially modified sequence.

As used herein, the term "xylose isomerase (XylA)-encoding gene (hereinafter, xylA)" means a polynucleotide encoding the above described XylA.

The gene may include a nucleotide sequence of SEQ ID NO: 3, a nucleotide sequence which can hybridize with a probe derived from the nucleotide sequence of SEQ ID NO: 3 under "stringent conditions", or a nucleotide sequence, in which one nucleotide or several nucleotides is/are substituted, deleted, inserted, or added at one or more positions of the nucleotide sequence of SEQ ID NO: 3. As long as it is able to maintain or enhance the XylA activity, the gene may include a nucleotide sequence having 80% or more, specifically 90% or more, more specifically 95% or more, much more specifically 97% or more homology with the nucleotide sequence of SEQ ID NO: 3, a nucleotide sequence substituted with codons favored by host cells, a nucleotide sequence of which N-terminus or C-terminus is extended or eliminated, or a nucleotide sequence of which start codon is modified to control expression level, and thus the gene is not particularly limited thereto.

As used herein, the term "xylulokinase (XylB)-encoding gene thereinafter, xylB)" means a polynucleotide encoding the above described XylB.

The gene may include a nucleotide sequence of SEQ ID NO: 4, a nucleotide sequence which can hybridize with a probe derived from the nucleotide sequence of SEQ ID NO: 4 under "stringent conditions", or a nucleotide sequence, in which one nucleotide or several nucleotides is/are substituted, deleted, inserted, or added at one or more positions of the nucleotide sequence of SEQ ID NO: 4. As long as it is able to maintain or enhance the XylB activity, the gene may include a nucleotide sequence having 80% or more, specifically 90% or more, more specifically 95% or more, much more specifically 97% or more homology with the nucleotide sequence of SEQ ID NO: 4, a nucleotide sequence substituted with codons favored by host cells, a nucleotide sequence of which N-terminus or C-terminus is extended or eliminated, or a nucleotide sequence of which start codon is modified to control expression level, and thus the gene is not particularly limited thereto.

As used herein, the term "stringent conditions" means conditions which permit a specific hybridization between polynucleotides, for example, hybridization in a hybridization buffer at 65° C. (3.5×SSC (0.15 M NaCl/0.15 M sodium citrate, pH 7.0), 0.02% Ficoll, 0.02% polyvinylpyrrolidone, 0.02% bovine serum albumin, 0.5% SDS, 2 mM EDTA, 2.5 mM $NaH_2PO_4$, pH 7), and a detailed description is disclosed in the related art (Molecular Cloning (A Laboratory Manual, J. Sambrook et al., Editors, 2nd Edition, Cold Spring Harbor Laboratory press, Cold Spring Harbor, N.Y., 1989) or Current Protocols in Molecular Biology (F. M. Ausubel et al., Editors, John Wiley & Sons, Inc., New York).

As described above, introduction of XylA and XylB activities into *Corynebacterium* sp. microorganism may be carried out by various methods well known in the art. For example, there are a method of inserting a polynucleotide including the nucleotide sequences encoding XylA and XylB into a chromosome, a method of introducing a vector system including the polynucleotide into the microorganism, a method of introducing a potent promoter to upstream of the nucleotide sequences encoding XylA and XylB, a method of introducing xylA and xylB with a modified promoter, or a method of introducing a modified nucleotide sequences encoding XylA and XylB, or the like. More specifically, if the nucleotide sequences encoding XylA and XylB are introduced, *Corynebacterium* ammoniagenes-derived pcj7 promoter (Korean Patent No. 10-0620092) can be used as a promoter for controlling the expression thereof. In one embodiment of the present invention, acquisition of xylose-utilizing ability was confirmed as the activity of the foreign gene absent in the parent strain was observed by introduction of an expression vector or chromosomal insertion.

As used herein, the term "vector" refers to a DNA product having a nucleotide sequence of a polynucleotide encoding the target protein, which is operably linked to a suitable regulatory sequence to express the target protein in a suitable host. The regulatory sequence includes a promoter capable of initiating transcription, an arbitrary operator sequence for regulating transcription, a sequence encoding an appropriate mRNA ribosome binding site, and sequences for regulating the termination of transcription and translation. Once transformed into a suitable host, the vector may replicate or function independently of the host genome, or may integrate into the genome itself.

The vector that is used in the present invention is not specifically limited and may be any vector known in the art, as long as it can replicate in a host. Example of the vector typically used may be natural or recombinant plasmid, cosmid, virus and bacteriophage. For example, as the phage vector or the cosmid vector, pWE15, M13, λMBL3, λMBL4, λIXII, λASHII, λAPII, λt10, λt11, Charon4A, Charon21A or the like may be used. As the plasmid vector, pBR type, pUC type, pBluescriptII type, pGEM type, pTZ type, pCL type, pET type or the like may be used.

The vector useful in the present invention is not particularly limited, and the known expression vector may be used. Specifically, pACYC177, pACYC184, pCL, pECCG117, pUC19, pBR322, pMW118, pCC1BAC vector or the like may be used.

Furthermore, the vector used in the present invention may be a vector capable of transforming host cells, to insert the polynucleotide encoding the target protein into the chromosome of the host cell. Specific examples of the vector include, but are not limited to, the shuttle vector pECCG112 that can self-replicate in both directions in *E. coli* and or Coryne-type bacteria (Korean Patent No. 10-0057684).

As used herein, the term "transformation" means a series of operations for introducing a vector including a polynucleotide encoding a target protein into a host cell so as to express the protein encoded by the polynucleotide in the host cell. The polynucleotide to be introduced into the host cell may have any form, as long as it is introduced into the host cell and expressed therein. For example, the polynucleotide may be introduced into a host cell in the form of an expression cassette that is a structure including all elements (a promoter operably linked to the polynucleotide, a transcription termination signal, a ribosome binding site, a translation termination signal, etc.) required for self-expression. The expression cassette may be in the form of a self-replicable expression vector. In addition, the polynucleotide itself may be introduced into a host cell to be operably linked to a sequence required for expression in the host cell.

The host cell may be any one of prokaryotic microorganisms, as long as it is able to produce L-lysine. Examples of the host cell may include *Providencia* sp., *Corynebacterium* sp. and *Brevibacterium* sp. microorganism, specifically, *Corynebacterium* sp. microorganism, and more specifically *Corynebacterium glutamicum*. In one embodiment of the present invention, when KCCM11016P, KCCM10770P, KFCC10750, and CJ3P as *Corynebacterium* sp. microorganism having no xylose-utilizing ability are introduced with XlyA and XlyB derived from *Erwinia carotovora*, they are provided with xylose-utilizing ability, and as a result, L-amino acid such as L-lysine can be produced by utilizing xylose as a carbon source (Tables 1 to 6).

*Corynebacterium* sp. microorganism having an ability to produce L-lysine may be a variant resistant to an L-lysine analogue. The L-lysine analogue inhibits growth of Coryneform microorganism, but this inhibition is fully or partially desensitized when L-lysine coexists in a medium. Examples of the L-lysine analogue include, but are not limited to, oxa-L-lysine, L-lysine hydroxamate, S-(2-aminoethyl)-L-cysteine(AEC), γ-methyl L-lysine, α-chlorocaprolactam or the like. Variant having resistance to these L-lysine analogues can be obtained by a conventional artificial mutagenesis treatment to Coryneform microorganism. In addition, when genetic manipulation is conducted to induce L-lysine-producing microorganism, it can be achieved by improving the expression of one or more of genes encoding enzymes involved in the L-lysine biosynthetic system. Examples of these genes may include dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh), phosphoenolpyruvate carboxylase gene (ppc), aspartate semialdehyde dehydrogenase gene (asd) and aspartase gene (aspA), but are not limited thereto.

As used herein, the term "L-lysine" is one of the basic α-amino acids, is an essential amino acid that is not synthesized in the body, is one of the L-amino acids, and has a chemical formula of $NH_2(CH_2)_4CH(NH_2)COOH$. L-lysine is synthesized from oxaloacetate through L-lysine biosynthetic pathway, and NADPH-dependent reductase catalyzes an intermediate process for L-lysine biosynthesis. During the biosynthetic process of 1 molecule of L-lysine, 3 molecules of NADPH are directly consumed by the corresponding enzymes, and 1 molecule of NADPH is indirectly used.

As used herein, the term "*Corynebacterium* sp. microorganism capable of producing L-lysine" means *Corynebacterium* sp. microorganism modified to produce L-lysine from xylose, which is prepared by introducing genes encoding the enzymes involved in the xylose metabolism and not found in the *Corynebacterium* sp. microorganism. The *Corynebacterium* sp. microorganism may be, but is not particularly limited to, *Corynebacterium glutamicum*, and the enzymes involved in the xylose metabolism may be, but are not particularly limited to, XylA and XylB.

In this regard, the host cell may be *Corynebacterium* sp. microorganism, in which expressions of one or more of the genes encoding enzymes involved in the L-lysine biosynthetic system are improved, and the genes encoding enzymes involved in the L-lysine biosynthetic system may be, but are not limited to, dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh), phosphoenolpyruvate carboxylase gene (ppc), aspartate semialdehyde dehydrogenase gene (asd), aspartase gene (aspA) or the like.

In addition, the host cell may be a mutant strain resistant to an L-lysine analogue. The mutant strain may be obtained by mutation of *Corynebacterium* sp. microorganism. The L-lysine analogue inhibits growth of Coryneform microorganism, but this inhibition is fully or partially desensitized when L-lysine coexists in a medium. Examples of the L-lysine analogue may be, but are not particularly limited to, preferably oxa-L-lysine, L-lysine hydroxamate, S-(2-aminoethyl)-L-cysteine (AEC), γ-methyl L-lysine, α-chlorocaprolactam or the like.

Meanwhile, in the present invention, activities of the known enzymes involved in the L-lysine biosynthesis may be additionally controlled in order to further improve the L-lysine production. Specifically, in the present invention, asd, dapB, and ddh genes, each encoding aspartate semialdehyde dehydrogenase, dihydrodipicolinate reductase and diaminopimelate dehydrogenase enzymes, are overexpressed to additionally control activities of the enzymes, thereby improving the L-lysine production.

According to one embodiment of the present invention, the present inventors selected *Erwinia carotovora* (SCRI1043)-derived ECA0097(xylA) (SEQ ID NO: 1) and ECA0096 (xylB) (SEQ ID NO: 2) as suitable genes encoding XylA and XylB to introduce into *Corynebacterium* sp. microorganism (Example 1), and they cloned the selected genes encoding XylA and XylB so as to construct an expression vector pECCG122-pcj7-xylA-xylB (hereinafter, pECCG122-pcj7-xylAB(Er)) expressing xylA and xylB (hereinafter, xylAB (Er)) at the same time. The expression vector was introduced into *Corynebacterium glutamicum* KCCM11016P (this microorganism was disclosed as KFCC10881, and re-deposited to an International Depositary Authority under the Budapest Treaty with Accession No. KCCM11016P. Korean Patent Nos. 10-0159812 and 10-0397322) to prepare a transformant overexpressing xylAB(Er). It was confirmed that the prepared transformant grows by utilizing xylose as a carbon source (FIG. 2), and produces L-lysine by utilizing each of glucose and xylose, or by utilizing glucose and xylose at the same time (Table 1). In addition, in order to express xylAB (Er) on the chromosome, a recombinant vector for chromosomal insertion, pDZTn-pcj7-xylAB(Er) was constructed, and transformed into KCCM11016P, and through second crossover, a transformant KCCM11016P-pcj7-xylAB(Er) having xylAB(Er) operably linked to pcj7 promoter inside the transposon on the chromosome was constructed. It was also confirmed that the transformant grows by utilizing xylose as a carbon source (FIG. 3), and produces L-lysine by utilizing each of glucose and xylose, or by utilizing glucose and xylose at the same time (Table 2). Furthermore, in order to compare the effects of improving xylose-utilizing ability between introduction of the previously reported *E. coli*-derived xylAB (hereinafter, xylAB(Ec)) and introduction of *Erwinia carotovora*-derived xylAB(Er) of the present invention, a strain (KCCM11016P-pcj7-xylAB(Ec)) was prepared by introducing xylAB(Ec) into KCCM11016P, and its xylose-utilizing ability and L-lysine production characteristics were compared with those of the prepared KCCM11016P-pcj7-xylAB (Er). As a result, it was found that xylose consumption rate of KCCM11016P-pcj7-xylAB(Er) was remarkably increased, compared to that of KCCM11016P-pcj7-xylAB(Ec), indicating improvement in fermentative production of L-lysine (Table 3). In addition, in order to confirm whether various *Corynebacterium* sp. microorganisms show the same results, pDZTn-pcj7-xylAB(Er) was introduced to an L-lysine-producing strain KCCM10770P to prepare a transformant KCCM10770P-pcj7-xylAB(Er), and it was confirmed that the transformant is able to produce L-lysine by utilizing each of glucose and xylose, or by utilizing glucose and xylose at the same time (Table 4). pDZTn-pcj7-xylAB(Er) was also introduced into another L-lysine-producing strain KFCC10750 (this microorganism was disclosed as KFCC10750, and re-deposited to an International Depositary Authority under the Budapest Treaty with Accession No. KCCM11347P, Korean Patent No. 10-0073610) to prepare a transformant KFCC10750-pcj7-xylAB(Er). It was also confirmed that this transformant is able to produce L-lysine by utilizing each of glucose and xylose, or by utilizing glucose and xylose at the same time (Table 5). Further, pDZTn-pcj7-xylAB(Er) was also introduced into the other L-lysine-producing strain CJ3P to prepare a transformant CJ3P-pcj7-xylAB(Er). It was also confirmed that this transformant is able to produce L-lysine by utilizing each of glucose and xylose, or by utilizing glucose and xylose at the same time (Table 6).

Accordingly, the present inventors designated the transformant as "CA01-2195", which grows by utilizing xylose in a medium and also produces L-lysine by utilizing xylose and glucose in the medium, and deposited it under the Budapest Treaty at the Korean Culture Center of Microorganisms (KCCM, located on Hongjae 1-Dong, Seodaemun-Gu, Seoul, Korea) on Dec. 29, 2011 with Accession No. KCCM11242P. That is, this deposit is recognized by an International Depositary Authority under the Budapest Treaty.

In another aspect, the present invention provides a method for producing L-lysine, including the steps of (i) culturing the modified *Corynebacterium* sp. microorganism able to produce L-lysine by utilizing xylose in a culture medium containing xylose as a carbon source so as to obtain a culture broth; and (ii) recovering L-lysine from the culture broth.

As used herein, the term "culturing" means that a microorganism is cultured under artificially controlled environmental conditions. In the present invention, the method for culturing *Corynebacterium* sp. microorganism may be conducted using a method widely known in the art. Specifically, examples of the culturing method include batch process, fed batch or repeated fed batch process in a continuous manner, but are not limited thereto.

The medium used for the culture has to meet the requirements of a specific microorganism in a proper manner while controlling temperature, pH, etc. under aerobic conditions in a typical medium containing a proper carbon source, nitrogen source, amino acids, vitamins, etc. The culture media for *Corynebacterium* strain are disclosed (e.g., Manual of Methods for General Bacteriology, American Society for Bacteriology, Washington D.C., USA, 1981). Possible carbon sources may include sugars and carbohydrates such as sucrose, lactose, fructose, maltose, starch, and cellulose, in addition to a mixture of glucose and xylose as a main carbon source, oils and fats such as soy bean oil, sunflower oil, castor oil, and coconut fat, fatty acids such as palmitic acid, stearic acid, and linoleic acid, alcohols such as glycerol and ethanol, and organic acids such as acetic acid. These substances may be used individually or as mixtures. Possible nitrogen sources may include inorganic nitrogen sources such as ammonia, ammonium sulfate, ammonium chloride, ammonium acetate, ammonium phosphate, ammonium carbonate and ammonium nitrate; amino acids such as glutamic acid, methionine, and glutamine; and organic nitrogen sources such as peptone, NZ-amine, meat extract, yeast extract, malt extract, corn steep liquor, casein hydrolysates, fish or decomposition products thereof, and defatted soybean cake or decomposition products thereof. These nitrogen sources may be used individually or in combination. The medium may include potassium dihydrogen phosphate, dipotassium hydrogen phosphate or the corresponding sodium-containing salts as phosphorus sources. Possible phosphorus sources may include potassium dihydrogen phosphate, dipotassium hydrogen phosphate or the corresponding sodium-containing salts. Further, inorganic compounds such as sodium chloride, calcium chloride, iron chloride, magnesium sulfate, iron sulfate, manganese sulfate and calcium carbonate may be used. In addition to the above substances, essential growth substances, such as amino acids and vitamins, may be included.

Appropriate precursors may be also added to the culture media. The above-mentioned substances may be suitably added to the culture medium in batch, fed-batch or continuous mode during cultivation, but are not particularly limited thereto. pH of the culture may be adjusted by suitably adding basic compounds such as sodium hydroxide, potassium hydroxide, and ammonia, or acidic compounds such as phosphoric acid and sulfuric acid.

An anti-foaming agent such as fatty acid polyglycol esters may be used to suppress the development of foam. In order to maintain aerobic condition, oxygen or oxygen-containing gas (e.g., air) may be introduced into the culture broth. The temperature of the culture broth is normally 27° C. to 37° C., specifically 30° C. to 35° C. The cultivation may be continued until the production of L-lysine reaches a desired level. This objective may be normally achieved within 10 to 100 hours. L-lysine may be released into the culture medium or included within the cells.

Furthermore, the step of recovering L-lysine from the culture broth may be performed by a known method known in the art. Specifically, the known method for recovering L-lysine is, but not particularly limited to, specifically centrifugation, filtration, extraction, spraying, drying, evaporation, precipitation, crystallization, electrophoresis, differential solubility (e.g., ammonium sulfate precipitation), chromatography (e.g., ion exchange, affinity, hydrophobic, and size exclusion) or the like.

Hereinafter, the constitutions and effects of the present invention will be described in more detail with reference to Examples. However, these Examples are for illustrative purposes only, and the scope of the invention is not intended to be limited by these Examples.

Example 1

Selection of Foreign Gene

*Erwinia carotovora* (SCRI1043)-derived ECA0097(xylA) (amino acid: SEQ ID NO: 1, nucleotide: SEQ ID NO: 3) and ECA0096(xylB) (amino acid: SEQ ID NO: 2, nucleotide: SEQ ID NO: 4) were selected as foreign genes to prepare a modified *Corynebacterium* sp. microorganism provided with a xylose-utilizing ability.

Example 2

Construction of *Erwinia carotovora*-Derived xylAB Expressing Vector

*Erwinia carotovora*-derived XylA and XylB-encoding genes selected in Example 1 are located close to each other. Information (Accession NO. BX950851) about xylA and xylB(Er) and surrounding nucleotide sequence was obtained from US NIH GenBank, and based on the obtained nucleotide sequence, primers for amplification of *Erwinia carotovora*-derived xylAB(Er) were synthesized.

```
SEQ ID NO: 5:
5'-ACACATATGCAAGCCTATTTTGAACAGATC-3'

SEQ ID NO: 6:
5'-AGAACTAGTGCCTTTTGGTGGTGTTTAAGT-3'
```

In order to obtain the xylAB(Er) fragment, PCR was conducted using chromosomal DNA of *Erwinia carotovora* strain SCRI1043 as a template and a pair of primers (SEQ ID NOs: 5 and 6). PfuUltra™ high-fidelity DNA polymerase (Stratagene) was used as the polymerase, and PCR was conducted with denaturation at 94° C. for 5 minutes, followed by repeating the cycle 30 times including denaturation at 94° C. for 30 seconds, annealing at 56° C. for 30 seconds and polymerization at 72° C. for 3 minutes, and then polymerization at 72° C. for 7 minutes. As a result, a gene fragment of 3122 bp containing xylAB(Er) (SEQ ID NO: 17) of 2844 bp was obtained (SEQ ID NO: 18). In order to obtain *Corynebacterium* ammoniagenes-derived pcj7 promoter (KR0620092), PCR was conducted using genomic DNA of *Corynebacterium* ammoniagenes CJHB100 (KR0620092) as a template and a pair of primers (SEQ ID NOs: 15 and 16). PfuUltra™ high-fidelity DNA polymerase (Stratagene) was used as the polymerase, and PCR was conducted with denaturation at 94° C. for 5 minutes, followed by repeating the cycle 30 times including denaturation at 94° C. for 30 seconds, annealing at 56° C. for 30 seconds and polymerization at 72° C. for 1 minute, and then polymerization at 72° C. for 7 minutes. As a result, a polynucleotide of 318 bp was obtained (SEQ ID NO: 14).

```
SEQ ID NO: 15:
5'-AATCTAGAAACATCCCAGCGCTA-3'

SEQ ID NO: 16:
5'-AAACTAGTCATATGTGTTTCCTTTCGTTG-3'
``` pcj7 was cloned into *E. coli-Corynebacterium* shuttle vector pECCG122 using restriction enzymes, XbaI and SpeI, and then xylAB(Er) fragment was cloned using NdeI and SpeI, thereby obtaining a pECCG122-pcj7-xylAB(Er) vector (FIG. 1). FIG. 1 is a cleavage map of the expression vector pECCG122-pcj7-xylAB(Er) of the present invention.

Example 3

Development of L-Lysine-Producing Strain Introduced with *Erwinia carotovora*-Derived xylAB and Examination of Xylose-Utilizing Ability Each expression vector pECCG122-pcj7-xylAB(Er) obtained in Example 2 was introduced into *Corynebacterium glutamicum* KCCM11016P (Korean Patent Nos. 10-0159812 and 10-0397322) to prepare a xylAB(Er)-expressing transformant, *Corynebacterium glutamicum* CA01-2195.

In order to compare the xylose-utilizing ability between KCCM11016P and CA01-2195, the strains were cultured in a seed medium containing glucose or xylose as a carbon source and their growth characteristics were compared. They were also cultured in a production medium containing glucose or xylose as a carbon source and their L-lysine production characteristics were compared.

Figure 2:
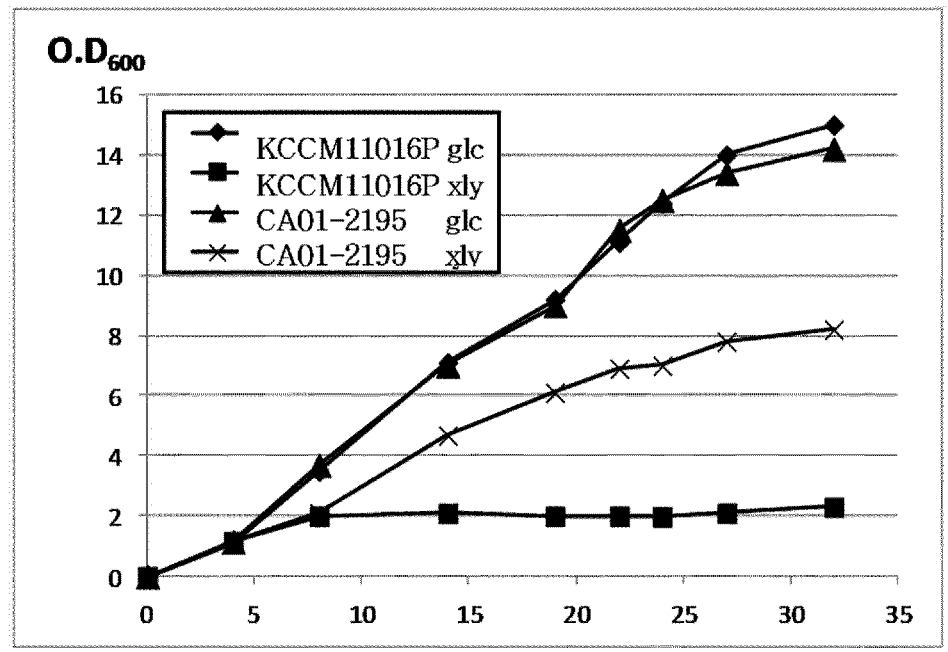
FIG. 2 shows a graph representing growth characteristics of a parent strain and a transformant introduced with the expression vector according to a carbon source contained in a medium.

First, in order to compare the growth characteristics, the strains were inoculated in 25 ml of seed medium [carbon source (glucose or xylose) 10 g/l, peptone 10 g/l, yeast extract 10 g/l, urea 5 g/l, $KH_2PO_4$ 4 g/l, $K_2HPO_4$ 8 g/l, $MgSO_4 7H_2O$ 0.5 g/l, biotin 100 µg/l, thiamine-HCl 1 mg/l, pH 7.0], respectively. Absorbance (OD600) of the culture broth was measured while culturing the strains at 30° C. for 32 hours, and compared to each other (FIG. 2). FIG. 2 is a graph showing growth characteristics of KCCM11016P and CA01-2195 according to carbon source contained in the medium, in which (♦) indicates KCCM11016P cultured in the medium containing glucose, (■) indicates KCCM11016P cultured in the medium containing xylose, (▲) indicates CA01-2195 cultured in the medium containing glucose, and (×) indicates CA01-2195 cultured in the medium containing xylose.

As shown in FIG. 2, there was no difference in growth characteristics between KCCM11016P and CA01-2195 in the seed medium containing glucose as a carbon source. However, in the seed medium containing xylose as a carbon source, CA01-2195 grew to a certain level whereas KCCM11016P hardly grew. Therefore, it can be seen that CA01-2195 is able to grow by utilizing xylose contained in the medium as a sole carbon source.

Next, to compare L-lysine production characteristics between KCCM11016P and CA01-2195, 1 ml of seed culture broth was inoculated in 24 ml of production medium [carbon source, $(NH_4)_2SO_4$ 40 g/l, soybean protein 2.5 g/l, corn steep solids 5 g/l, urea 3 g/l, $KH_2PO_4$ 1 g/l, $MgSO_4 7H_2O$ 0.5 g/l, biotin 100 µg/l, thiamine-HCl 1 mg/l, $CaCO_3$ 30 g/l, pH 7.0], and cultured at 35° C. and 200 rpm for 72 hours. At this time, glucose 100 g/l, glucose 50 g/l+xylose 50 g/l, and glucose 70 g/l+xylose 30 g/l were determined to be used as the carbon source. Next, concentration of L-lysine, concentration of residual xylose, and concentration of residual glucose in each culture broth were measured and compared (Table 1).

TABLE 1

| | Glucose 100 g/l | | | Glucose 50 g/l + Xylose 50 g/l | | | Glucose 70 g/l + Xylose 30 g/l | | |
|---|---|---|---|---|---|---|---|---|---|
| Strain | L-lysine | R.X | R.G | L-lysine | R.X | R.G | L-lysine | R.X | R.G |
| KCCM11016P | 42 | — | 0 | 21 | 50 | 0 | 29 | 30 | 0 |
| CA01-2195 | 42 | — | 0 | 40 | 0 | 0 | 41 | 0 | 0 |

R.X: residual xylose (concentration of residual xylose after reaction termination) (unit: g/l)
R.G: residual glucose (concentration of residual glucose after reaction termination)

As shown in Table 1, when the medium containing no xylose (glucose 100 g/l) was used, concentration of L-lysine produced in the parent strain was equivalent to that of CA01-2195. However, when the medium containing xylose (glucose 50 g/l+xylose 50 g/l, and glucose 70 g/l+xylose 30 g/l) was used, CA01-2195 produced L-lysine by consuming both glucose and xylose whereas the parent strain produced L-lysine by consuming no xylose but glucose only.

This result indicates that *Corynebacterium* sp. microorganism having no xylose-utilizing ability is able to consume xylose by introducing with *Erwinia carotovora*-derived xylAB.

Example 4

Construction of Recombinant Vector for Chromosomal Insertion of *Erwinia carotovora*-Derived xylAB (pDZTn-pcj7-xylAB(Er)) and Recombinant Vector for Chromosomal Insertion of *E. coli*-Derived xylAB (pDZTn-pcj7-xylAB(Ec))

To express the xylAB(Er) on chromosome, a recombinant vector pDZTn-pcj7-xylAB(Er) for chromosomal insertion was constructed. To obtain the pcj7-xylAB(Er) fragment, PCR was conducted using pECCG122-pcj7-xylAB(Er) obtained in Example as a template and a pair of primers (SEQ ID NOs: 7 and 8). PfuUltra™ high-fidelity DNA polymerase (Stratagene) was used as the polymerase, and PCR was conducted with denaturation at 94° C. for 5 minutes, followed by repeating the cycle 30 times including denaturation at 94° C. for 30 seconds, annealing at 56° C. for 30 seconds and polymerization at 72° C. for 3 minutes, and then polymerization at 72° C. for 7 minutes. As a result, a gene fragment of 3440 bp was obtained (SEQ ID NO: 9). Consequently, pcj7-xylAB (Er) of 3440 bp was cloned into pDZTn vector (Korean Patent No. 10-1126041) treated with restriction enzyme SpeI using a BD In-Fusion kit, thereby obtaining a pDZTn-pcj7-xylAB (Er) recombinant vector.

```
SEQ ID NO: 7:
5'-GAGTTCCTCGAGACTAGTAGAAACATCCCAGCGCTA-3'

SEQ ID NO 8:
5'-GATGTCGGGCCCACTAGGCCTTTTTGGTGGTGTTTA-3'
```

Next, to express *E. coli*-derived xylAB on chromosome, recombinant pDZTn-pcj7-xylAB(Ec) for chromosomal insertion was constructed. To obtain pcj7 promoter, PCR was conducted using the pcj7 fragment obtained in Example 2 as a template and a pair of primers (SEQ ID NOs: 7 and 10). PfuUltra™ high-fidelity DNA polymerase (Stratagene) was used as the polymerase, and PCR was conducted with denaturation at 94° C. for 5 minutes, followed by repeating the cycle 30 times including denaturation at 94° C. for 30 seconds, annealing at 56° C. for 30 seconds and polymerization at 72° C. for 1 minute, and then polymerization at 72° C. for 7 minutes. As a result, a gene fragment of 318 bp was obtained. To obtain xylAB(Ec) fragment, PCR was conducted using chromosomal DNA of *E. coli* K12 as a template and a pair of primers (SEQ ID NOs: 11 and 12). PfuUltra™ high-fidelity DNA polymerase (Stratagene) was used as the polymerase, and PCR was conducted with denaturation at 94° C. for 5 minutes, followed by repeating the cycle 30 times including denaturation at 94° C. for 30 seconds, annealing at 56° C. for 30 seconds and polymerization at 72° C. for 3 minutes, and then polymerization at 72° C. for 7 minutes. As a result, a xylAB(Ec) fragment of 3145 bp was obtained (SEQ ID NO: 13). Consequently, the PCR products of pcj7 region of 318 bp and xylAB(Ec) of 3145 bp were cloned into pDZTn vector treated with restriction enzyme SpeI using a BD In-Fusion kit, thereby a final pDZTn-pcj7-xylAB(Ec) recombinant vector.

```
SEQ ID NO: 10:
5'-TCAAAATAGGCTTGCATGAGTGTTTCCTTTCGTTG-3'

SEQ ID NO: 11:
5'-CAACGAAAGGAAACACATGCAAGCCTATTTTGAC-3'

SEQ ID NO: 12:
5'-GATGTCGGGCCCACTAGTGCTGTCATTAACACGCCA-3'
```

Example 5

Development of L-Lysine-Producing Strain Inserted with *Erwinia*-Derived xylAB and Examination of Xylose-Utilizing Ability The prepared pDZTn-pcj7-xylAB(Er) vector was transformed into KCCM11016P, and through second crossover, a KCCM11016P-pcj7-xylAB(Er) strain having xylAB(Er) with substitution of one copy of pcj7 promoter inside the transposon on the chromosome was obtained.

To compare the xylose-utilizing ability between KCCM11016P-pcj7-xylAB(Er) and KCCM11016P, they were cultured in a seed medium containing glucose or xylose as a carbon source and their growth characteristics were compared, and they were cultured in a production medium containing glucose or xylose as a carbon source and their L-lysine production characteristics were compared, in the same manner as in Example 3.

Figure 3:
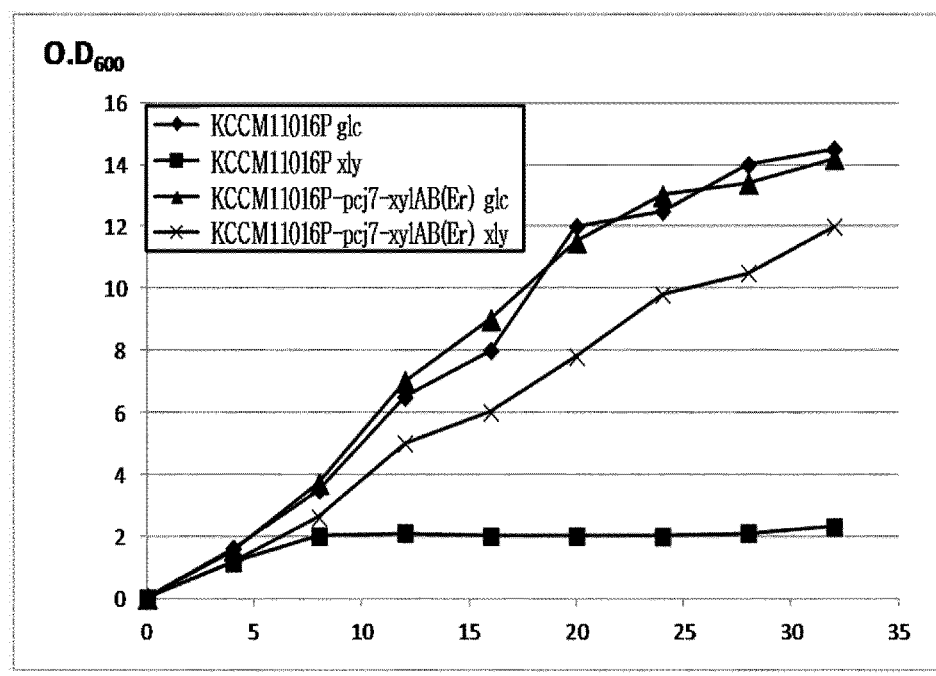
FIG. 3 shows a graph representing growth characteristics of a parent strain and a transformant of which pcj7-xylAB(Er) is inserted on chromosome according to a carbon source contained in a medium.

FIG. 3 is a graph showing growth characteristics of the strains according to carbon source contained in the medium, in which (♦) indicates KCCM11016P cultured in the medium containing glucose, (■) indicates KCCM11016P cultured in the medium containing xylose, (▲) indicates KCCM11016P-pcj7-xylAB(Er) cultured in the medium containing glucose, and (×) indicates KCCM11016P-pcj7-xylAB(Er) cultured in the medium containing xylose.

There was no difference in growth characteristics between KCCM11016P-pcj7-xylAB(Er) and KCCM11016P in the seed medium containing glucose as a carbon source. However, in the seed medium containing xylose as a carbon source, KCCM11016P-pcj7-xylAB(Er) grew to a certain level whereas KCCM111016P hardly grew. Therefore, it can be seen that when xylAB(Er) is inserted into the chromosome, the strain is able to grow by utilizing xylose contained in the medium.

Next, L-lysine production characteristics of KCCM11016P-pcj7-xylAB(Er) and KCCM11016P were examined and compared with each other (Table 2).

TABLE 2

| Strain | Glucose 100 g/l | | | Glucose 50 g/l + Xylose 50 g/l | | | Glucose 70 g/l + Xylose 30 g/l | | |
|---|---|---|---|---|---|---|---|---|---|
| | L-lysine | R.X | R.G | L-lysine | R.X | R.G | L-lysine | R.X | R.G |
| KCCM11016P | 43.0 | — | 0 | 22.6 | 50 | 0 | 29.2 | 30 | 0 |
| | 42.5 | — | 0 | 21.9 | 50 | 0 | 29.6 | 30 | 0 |
| KCCM11016P-pcj7-xylAB(Er) | 42.8 | — | 0 | 42.1 | 0 | 0 | 42.6 | 0 | 0 |
| | 43.1 | — | 0 | 42.0 | 0 | 0 | 42.2 | 0 | 0 |

R.X: residual xylose (concentration of residual xylose after reaction termination) (unit: g/l)
R.G. residual glucose (concentration of residual glucose after reaction termination)

As shown in Table 2, when the medium containing no xylose (glucose 100 g/l) was used, concentration of L-lysine produced in KCCM11016P was equivalent to that of KCCM11016P-pcj7-xylAB(Er). However, when the medium containing xylose (glucose 50 g/l+xylose 50 g/l, and glucose 70 g/l+xylose 30 g/l) was used, the KCCM11016P strain produced L-lysine by consuming only glucose whereas KCCM11016P-pcj7-xylAB(Er) produced L-lysine by consuming both glucose and xylose.

Example 6

Preparation of L-Lysine-Producing Strain Inserted with *E. coli*-Derived xylAB and Comparison of its Xylose-Utilizing Ability with that of KCCM11016P-pcj7-xylAB(Ec) Strain To compare the effects of improving xylose-utilizing ability between introduction of the previously reported *E. coli*-derived xylAB and introduction of *Erwinia carotovora*-derived XylAB of the present invention, a strain was prepared by introducing xylAB(Ec) into KCCM11016P, and its xylose-utilizing ability and L-lysine production characteristics were compared with those of the prepared KCCM11016P-pcj7-xylAB(Er).

To prepare a xylAB(Ec)-introduced strain, the pDZTn-pcj7-xylAB(Ec) recombinant vector prepared in Example 4 was transformed into KCCM11016P, and through second crossover, a KCCM11016P-pcj7-xylAB(Ec) strain having xylAB(Ec) operably linked to pcj7 promoter inside the transposon on the chromosome was obtained.

In the same manner as in example 3, to compare the xylose-utilizing ability between KCCM11016P-pcj7-xylAB(Er) and KCCM11016P-pcj7-xylAB(Ec), they were cultured in the production medium containing glucose 50 g/l+xylose 50 g/l as a carbon source, and their L-lysine production characteristics were compared, and to examine the xylose-utilizing ability, concentration of residual xylose in the culture broth was measured at 15 hours (Table 3).

TABLE 3

| | R.X (g/L) | | Lysine |
|---|---|---|---|
| | 45 h | 72 h | 72 h |
| KCCM11016P-pcj7-xylAB(Er) | 8.0 | 0 | 42.8 |
| | 7.2 | 0 | 42.2 |
| KCCM11016P-pcj7-xylAB(Ec) | 11.2 | 0 | 42.7 |
| | 12.1 | 0 | 42.4 |

R.X: residual xylose (concentration of residual xylose after reaction termination) (unit: g/l)

As shown in Table 3, the two strains showed equivalent L-lysine productivity. The xylose consumption rate of KCCM11016P-pcj7-xylAB(Er) was faster than that of KCCM11016P-pcj7-xylAB(Ec), indicating improvement in fermentation productivity. That is, this result indicates that introduction of *Erwinia carotovora*-derived xylAB (Er) of the present invention shows more excellent effect of improving L-lysine fermentation productivity than introduction of the previous *E. coli*-derived xylAB(Ec).

Example 7

Development of KCCM10770P-Derived Strain Inserted with *Erwinia carotovora*-Derived xylAB and Examination of Xylose-Utilizing Ability To examine whether xylAB(Er) introduction exhibits the same effect in other L-lysine-producing strains than KCCM11016P, pDZTn-pcj7-xylAB(Er) was introduced into an L-lysine-producing strain KCCM 10770P (Korean Patent No. 10-0924065) which was deposited to an International Depositary Authority under the Budapest Treaty. After introduction by an electric pulse method, a strain having xylAB (Er) with substitution of one copy of pcj7 promoter inside the transposon on the chromosome was obtained through second crossover, and the strain was named as *Corynebacterium glutamicum* KCCM10770P-pcj7-xylAB(Er).

Xylose-utilizing ability and L-lysine productivity of *Corynebacterium glutamicum* KCCM10770P and *Corynebacterium glutamicum* KCCM10770P-pcj7-xylAB(Er) of the present invention were measured in the same manner as in Example 3 (Table 4).

TABLE 4

| Strain | R.G | R.X | L-lysine |
|---|---|---|---|
| KCCM10770P | 0 | 50 | 23.8 |
| | 0 | 50 | 24.4 |
| KCCM10770P-pcj7-xylAB(Er) | 0 | 0 | 47.6 |
| | 0 | 0 | 47.5 |

R.X: residual xylose (concentration of residual xylose after reaction termination) (unit: g/l)
R.G: residual glucose (concentration of residual glucose after reaction termination)

As shown in Table 4, when the L-lysine-producing strain KCCM10770P was introduced with xylAB(Er), it completely consumed xylose, unlike the parent strain that cannot utilize xylose, and its L-lysine productivity was also increased.

This result supports that when *Erwinia carotovora*-derived xylAB is introduced into various *Corynebacterium* sp. microorganisms as well as *Corynebacterium* sp. microorganism specified by a certain Accession Number, they completely consume xylose as a carbon source, thereby efficiently producing amino acids such as L-lysine.

Example 8

Development of KFCC10750-Derived Strain Inserted with *Erwinia carotovora*-Derived xylAB and Examination of Xylose-Utilizing Ability To examine whether xylAB(Er) introduction exhibits the same effect in other L-lysine-producing strains than KCCM11016P, pDZTn-pcj7-xylAB(Er) was introduced into an L-lysine-producing strain KFCC10750 (Korean Patent No. 10-0073610). After introduction by an electric pulse method, a strain having xylAB(Er) with substitution of one copy of pcj7 promoter inside the transposon on the chromosome was obtained through second crossover, and the strain was named as *Corynebacterium glutamicum* KFCC10750-pcj7-xylAB(Er).

Xylose-utilizing ability and L-lysine productivity of *Corynebacterium glutamicum* KFCC10750 and *Corynebacterium glutamicum* KFCC10750-pcj7-xylAB(Er) of the present invention were measured in the same manner as in Example 3 (Table 5).

TABLE 5

| Strain | R.G | R.X | L-lysine |
|---|---|---|---|
| KFCC10750 | 0 | 50 | 19.7 |
|  | 0 | 50 | 18.8 |
| KFCC10750-pcj7-xylAB(Er) | 0 | 0 | 38.3 |
|  | 0 | 0 | 38.6 |

R.X: residual xylose (concentration of residual xylose after reaction termination) (unit: g/l)
R.G: residual glucose (concentration of residual glucose after reaction termination)

As shown in Table 5, when the L-lysine-producing strain KFCC10750 was introduced with xylAB(Er), it completely consumed xylose, unlike the parent strain that cannot utilize xylose, and its L-lysine productivity was also increased.

This result supports that when *Erwinia carotovora*-derived xylAB is introduced into various *Corynebacterium* sp. microorganisms as well as *Corynebacterium* sp. microorganism specified by a certain Accession Number, they completely consume xylose as a carbon source, thereby efficiently producing amino acids such as L-lysine.

Example 9

Development of CJ3P-Derived Strain Inserted with *Erwinia carotovora*-Derived xylAB and Examination of Xylose-Utilizing Ability To examine whether xylAB(Er) introduction exhibits the same effect in other L-lysine-producing strains than KCCM11016P, pDZTn-pcj7-xylAB(Er) was introduced into an L-lysine-producing strain CJ3P. CJ3P strain is a *Corynebacterium glutamicum* strain which has an ability to produce L-lysine by introduction of P458S, V59A, and T311I mutations into 3 types of genes, pyc, hom, and lysC of the wild-type strain, based on the technique reported by Binder et al. (Genome Biology 2102, 13:R40). After introduction by an electric pulse method, a strain having xylAB(Er) with substitution of one copy of pcj7 promoter inside the transposon on the chromosome was obtained through second crossover, and the strain was named as *Corynebacterium glutamicum* CJ3P-pcj7-xylAB(Er).

Xylose-utilizing ability and L-lysine productivity of *Corynebacterium glutamicum* CJ3P and *Corynebacterium glutamicum* CJ3P-pcj7-xylAB(Er) of the present invention were measured in the same manner as in Example 3 (Table 6).

TABLE 6

| Strain | R.G | R.X | L-lysine |
|---|---|---|---|
| CJ3P | 0 | 50 | 4.0 |
|  | 0 | 50 | 4.5 |
| CJ3P-pcj7-xylAB(Er) | 0 | 0 | 8.5 |
|  | 0 | 0 | 9.0 |

R.X: residual xylose (concentration of residual xylose after reaction termination) (unit: g/l)
R.G: residual glucose (concentration of residual glucose after reaction termination)

As shown in Table 6, when the L-lysine-producing strain CJ3P was introduced with xylAB(Er), it completely consumed xylose, unlike the parent strain that cannot utilize xylose, and its L-lysine productivity was also increased.

This result supports that when *Erwinia carotovora*-derived xylAB is introduced into various *Corynebacterium* sp. microorganisms as well as *Corynebacterium* sp. microorganism specified by a certain Accession Number, they completely consume xylose as a carbon source, thereby efficiently producing amino acids such as L-lysine.

Therefore, *Corynebacterium* sp. microorganism expressing xylAB(Er) is able to grow by utilizing xylose in a medium, and also able to produce L-lysine by utilizing xylose and glucose in a medium.

EFFECT OF THE INVENTION

When *Corynebacterium* sp. microorganism of the present invention able to produce L-lysine by utilizing xylose is used, L-lysine can be produced by using xylose as the second most abundant lignocellulosic carbohydrate in nature. Therefore, the microorganism can be widely used for the efficient and economical production of L-lysine.

What is claimed is:

1. A *Corynebacterium glutamicum* microorganism, wherein said microorganism is transformed with a polynucleotide encoding an *Erwinia carotovora* xylose isomerase (XylA) and a polynucleotide encoding an *Erwinia carotovora* xylulokinase (XylB), and wherein the microorganism expresses the *E. carotovora* XylA and *E. carotovora* XylB and can utilizes xylose when present in a culture medium to produce L-lysine.

2. The microorganism according to claim 1, wherein the *E. carotovora* XylA comprises the amino acid sequence of SEQ ID NO: 1, and the *E. carotovora* XylB comprises the amino acid sequence of SEQ ID NO: 2.

3. The microorganism according to claim 1, wherein the *E. carotovora* XylA is encoded by the polynucleotide sequence of SEQ ID NO: 3, and the *E. carotovora* XylB is encoded by the polynucleotide sequence of SEQ ID NO: 4.

4. The microorganism according to claim 1, wherein:
the polynucleotides encoding the *E. carotovora* XylA and *E. carotovora* XylB are integrated into the chromosome of the microorganism,
the polynucleotides encoding the *E. carotovora* XylA and *E. carotovora* XylB are present within a vector comprising a polynucleotide encoding XylA and XylB,
the polynucleotides encoding the *E. carotovora* XylA and *E. carotovora* XylB are operably linked to a heterologous promoter, or
a combination thereof.

5. A method for producing L-lysine, comprising the steps of:
(i) culturing the *Corynebacterium glutamicum* microorganism of claim 1 in a culture medium containing xylose as a carbon source so as to obtain a culture broth comprising L-lysine; and
(ii) recovering L-lysine from the culture broth.

6. The method according to claim 5, wherein the *E. carotovora* XylA comprises the amino acid sequence of SEQ ID NO: 1, and the *E. carotovora* XylB comprises the amino acid sequence of SEQ ID NO: 2.

7. The microorganism according to claim 1, wherein the *E. carotovora* XylA comprises an amino acid sequence having at least 97% amino acid sequence homology with the amino acid sequence of SEQ ID NO: 1 and has xylose isomerase activity, and wherein the *E. carotovora* XylB comprises an amino acid sequence having at least 97% amino acid sequence homology with the amino acid sequence of SEQ ID NO: 2 and has xylulokinase activity.

* * * * *